(12) United States Patent
Sanchini et al.

(10) Patent No.: US 11,186,719 B2
(45) Date of Patent: Nov. 30, 2021

(54) HEMICYANINE DYES

(71) Applicant: LI-COR, Inc., Lincoln, NE (US)

(72) Inventors: Silvano Sanchini, Lincoln, NE (US); Rose Skopp, Lincoln, NE (US); Vassil Elitzin, Lincoln, NE (US); Nisha Padhye, Lincoln, NE (US); Teresa Urlacher, Lincoln, NE (US)

(73) Assignee: LI-COR, INC., Lincoln, NE (US)

( * ) Notice: Subject to any disclaimer, the term of this patent is extended or adjusted under 35 U.S.C. 154(b) by 0 days.

(21) Appl. No.: 16/404,993

(22) Filed: May 7, 2019

(65) Prior Publication Data

US 2019/0338131 A1    Nov. 7, 2019

Related U.S. Application Data

(63) Continuation of application No. PCT/US2019/030631, filed on May 3, 2019.

(60) Provisional application No. 62/666,880, filed on May 4, 2018.

(51) Int. Cl.
   *C09B 23/01* (2006.01)
   *G01N 33/58* (2006.01)
   *C07D 209/14* (2006.01)
   *C07D 403/12* (2006.01)

(52) U.S. Cl.
   CPC ....... *C09B 23/0091* (2013.01); *G01N 33/582* (2013.01)

(58) Field of Classification Search
   CPC .. C09B 23/0091; C09B 23/145; C07D 209/14
   See application file for complete search history.

(56) References Cited

U.S. PATENT DOCUMENTS

| 3,955,984 | A | | 5/1976 | Kobayashi et al. |
| 4,268,622 | A | * | 5/1981 | Adachi ............... C09B 23/107 430/513 |
| 5,616,502 | A | | 4/1997 | Haugland et al. |

FOREIGN PATENT DOCUMENTS

| JP | 55161234 | 12/1980 |
| JP | 0511409 | 1/1993 |
| JP | 05142690 | 6/1993 |
| JP | 05313303 | 11/1993 |
| JP | 0643585 | 2/1994 |
| JP | 06102608 | 4/1994 |
| KR | 20110120679 | 11/2011 |
| WO | 2008054600 | 5/2008 |

OTHER PUBLICATIONS

Anderson et al. J. Am. Chem. Soc 1995, 117, 3889-3890. (Year: 1995).*
STNext Registry Database, Chemical Abstract Service, Registry No. 783256-38-2 [Entered STN: Nov. 17, 2004], (Year: 2004).*
International Application No. PCT/US2019/030631, International Search Report and Written Opinion dated Jul. 30, 2019, 14 pages.
Application No. PCT/US2019/030631, International Preliminary Report on Patentability, dated Nov. 19, 2020, 9 pages.

* cited by examiner

*Primary Examiner* — Amanda L. Aguirre
(74) *Attorney, Agent, or Firm* — Kilpatrick Townsend & Stockton LLP

(57) ABSTRACT

The present disclosure embodies compounds of Formula I, methods of use thereof, and kits thereof:

Formula I

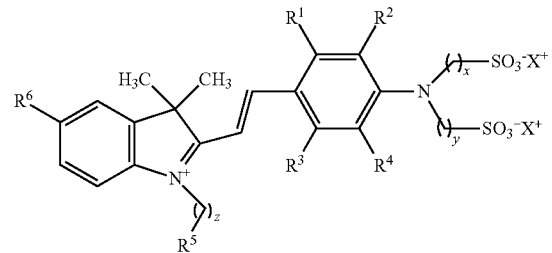

that are useful in connection with the detection of analytes of all types (e.g., biological molecules such as proteins, organic molecules, natural or synthetic molecules). The disclosure is particularly applicable to detection of proteins and nucleic acids using all types of membrane-based assays by techniques such as Western blotting, Dot blotting, Southern blotting, and Northern blotting.

19 Claims, 11 Drawing Sheets

Blue = SS2 Total Protein Stain
Red = β-Actin
Green = α-Tubulin
Pink = Total Protein Stain overlay Actin
Turquoise = Total Protein Stain overlay Tubulin

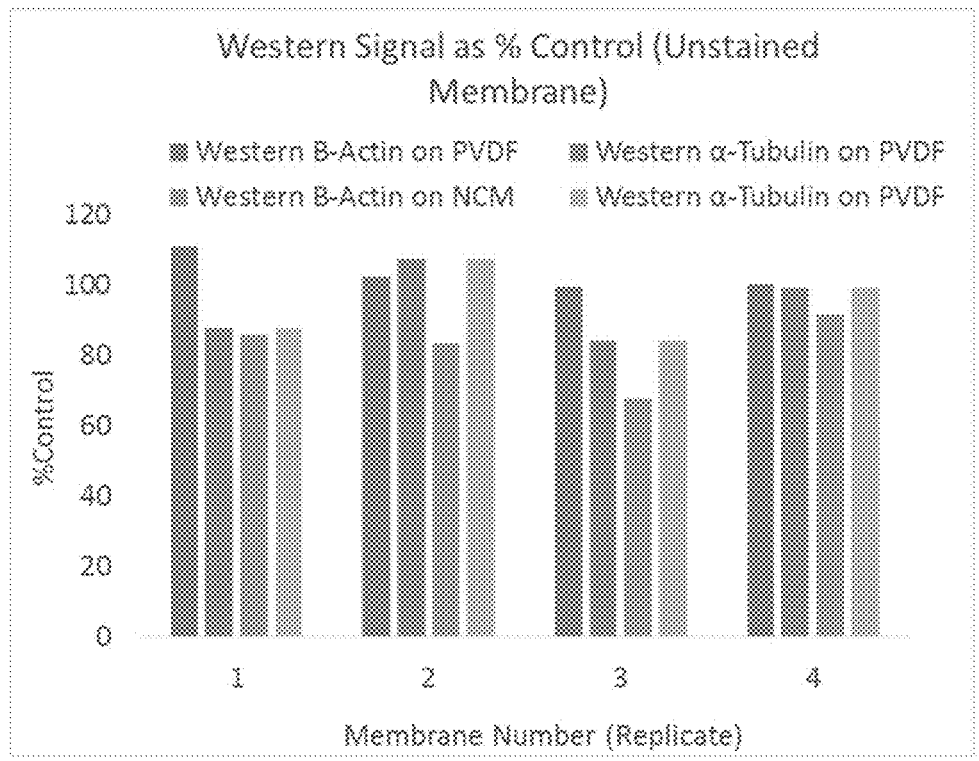
*FIG. 9B*
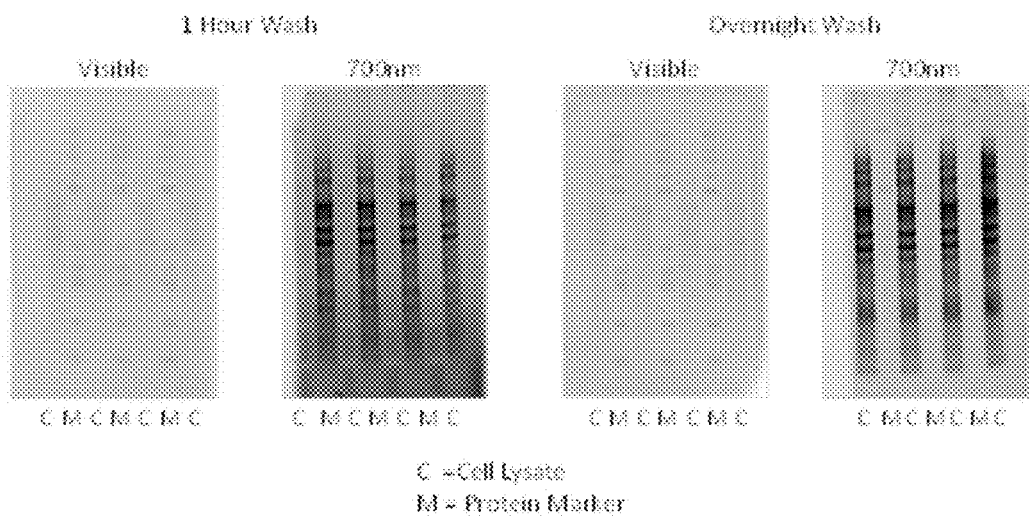
*FIG. 10A*  *FIG. 10B*  *FIG. 10C*  *FIG. 10D*

Saturated Signal
*FIG. 11A*
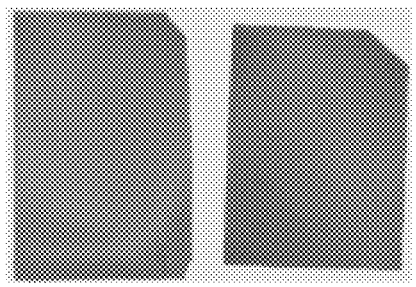
Background Staining
Saturated Signal
*FIG. 11B*
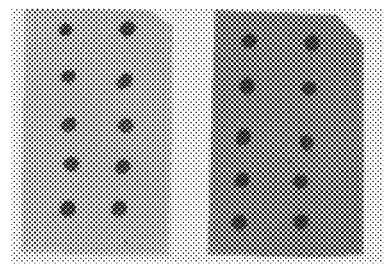
Fluorescent Signal
Odyssey Fc 600 Channel
Ex 530nm; Em 580nm
Auto Mode
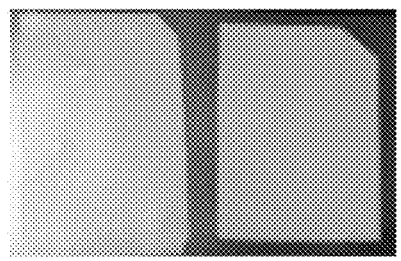
Visible Color
*FIG. 11C*
iPhone
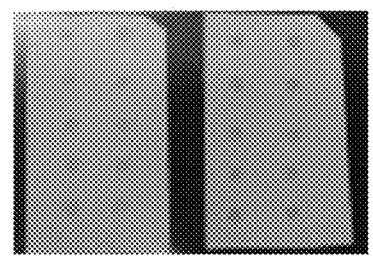
Visible Color
*FIG. 11D*

HEMICYANINE DYES

CROSS-REFERENCE TO RELATED APPLICATIONS

This application is a Continuation of PCT/US2019/030631 filed May 3, 2019, which claims priority to U.S. Provisional Patent Application No. 62/666,880, filed May 4, 2018, the disclosure of which is hereby incorporated by reference in its entirety for all purposes.

BACKGROUND OF THE INVENTION

Cyanine and hemicyanine dyes have been widely used for labeling ligands or biomolecules for a variety of applications such as DNA sequencing. More recently, these dyes have been used for optical imaging of dye-labeled biomolecules, either in vivo or in vitro. Cyanine and hemicyanine dyes are used in biological applications because, among other reasons, many of these dyes fluoresce in the near-infrared (NIR) region of the spectrum (550-1000 nm). This makes cyanine and hemicyanine dyes less susceptible to interference from autofluorescence of biomolecules.

Other advantages of cyanine and hemicyanine dyes include, for example: 1) cyanine and hemicyanine dyes strongly absorb and fluoresce light; 2) many cyanine and hemicyanine dyes do not rapidly bleach under a fluorescence microscope; 3) cyanine and hemicyanine dye derivatives can be made that are effective coupling reagents; 4) many structures and synthetic procedures are available, and these classes of dyes are versatile; and 5) cyanine and hemicyanine dyes are relatively small (a typical molecular weight is about 1,000 daltons), so they do not cause appreciable steric interference in a way that might reduce the ability of a labeled biomolecule to reach its binding site or carry out its function.

U.S. Pat. No. 4,268,622 to Fuji Photo Film discloses a silver halide photographic light-sensitive material having on a support a hydrophilic colloidal layer containing a basic polymer, and at least one styryl or butadienyl dye having at least three sulfo groups in the dye molecule. The dye molecule is used to prevent halation or a blurring effect when light is reflected back through the emulsion layer.

U.S. Pat. No. 5,616,502 to Molecular Probes, Inc. discloses the use of a variety of merocyanine dyes and substituted merocyanine dyes for detecting and quantifying polypeptides and proteins. The proteins can be detected in solution, gels and solid supports.

In view of the foregoing, there is a need for new and improved hemicyanine dyes for protein staining and bioconjugation. The present disclosure satisfies these and other needs.

BRIEF SUMMARY OF THE INVENTION

In one embodiment, the disclosure embodies a compound (a dye) of Formula I:

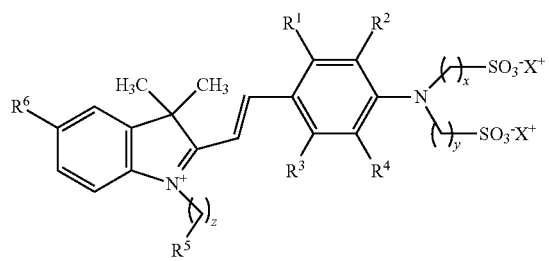

I wherein $R^1$, $R^2$, $R^3$, $R^4$, $R^5$ and $R^6$ are each a member independently selected from the group consisting of hydrogen, alkyl, alkenyl, halo, hydroxyl, alkoxy, amino, cyano, carboxyl, carboxylate, alkoxycarbonyl, amido, sulfonato, alkoxyalkyl, carboxyalkyl, alkoxycarbonylalkyl, sulfonatoalkyl, a functional group for conjugation to a biomolecule, and $R^7B$, wherein $R^7$ is a resultant attachment between the compound and a biomolecule after conjugation, wherein in Formula I, at least one of $R^1$, $R^2$, $R^3$, $R^4$, $R^5$ and $R^6$ is a functional group for conjugation or is $R^7B$;

B is a biomolecule;

x, y and z are each an integer independently selected from 1-10; and

X is hydrogen or a metal cation, wherein the compound has a balanced charge.

Suitable functional groups for conjugation to a biomolecule include, but are not limited to, an amine, a carbamate, a carboxylic acid, a carboxylate, a maleimide, an activated acyl, an activated ester, N-hydroxysuccinimidyl, a hydrazine, a hydrazide, a hydrazone, an azide, an alkyne, an aldehyde, a thiol, and protected groups thereof for conjugation to a molecule or biomolecule.

In another embodiment, the disclosure embodies a compound (a dye) of Formula I(a):

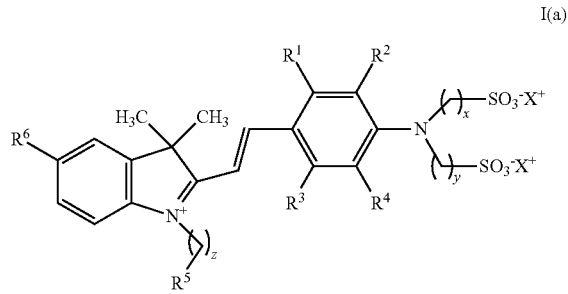

I(a)

wherein $R^1$, $R^2$, $R^3$, $R^4$, $R^5$ and $R^6$ are each a member independently selected from the group consisting of hydrogen, alkyl, alkenyl, halo, hydroxyl, alkoxy, amino, cyano, carboxyl, carboxylate, alkoxycarbonyl, amido, sulfonato, alkoxyalkyl, carboxyalkyl, alkoxycarbonylalkyl, sulfonatoalkyl;

x, y and z are each an integer independently selected from 1-10; and

X is hydrogen or a metal cation, wherein the compound has a balanced charge.

In another embodiment, the disclosure embodies an assay method for measuring an analyte in a sample, the method comprising:
  a) contacting the sample with a binding agent that binds to an analyte to form an analyte complex;
  b) contacting the sample with a compound of Formula I or I(a), wherein the compound of Formula I or I(a) reacts with the analyte complex to form a detectable agent; and
  c) upon excitation, detecting an optical signal from the detectable agent. The optical signal can be fluorescence.

In yet another embodiment, the disclosure embodies a method for detecting an analyte in a sample, the method comprising:
  a) combining the sample and a compound of Formula I or I(a),
  b) exciting the sample with light; and
  c) detecting fluorescence from the compound of Formula I or I(a), thereby detecting the analyte.

In still yet another embodiment, the disclosure embodies a method for detecting a target biomolecule in a sample, the method comprising:
  a) providing a sample that is suspected of containing a target analyte;
  b) providing a compound of Formula I or I(a) conjugated to a capture molecule, wherein the capture molecule is capable of interacting with the target analyte;
  c) contacting the sample with the capture molecule and the compound of Formula I or I(a) under conditions in which the capture molecule can bind to the target analyte, if present;
  d) applying a light source to the sample that excites the compound of Formula I or I(a); and detecting whether light is emitted from the conjugated compound of Formula I or I(a).

In one embodiment, the disclosure provides a method for staining and or detecting a protein, the method comprising:
  contacting a staining mixture that contains a compound or dye of Formula I or I(a) with a protein to form a combined mixture;
  incubating the combined mixture for a time sufficient for the compound or dye of Formula I or I(a) to associate with the protein to form a dye complex that gives an optical response upon illumination;
  illuminating the dye-protein complex; and
  detecting the optical response.

In still another embodiment, the disclosure embodies a kit for staining a protein in a sample, the kit comprising:
  a) a compound or dye or Formula I or I(a); and
  b) instructions for combining the compound of Formula I or I(a)a with a sample containing or thought to contain protein.

These and other objects, advantages and embodiments will become more apparent when read with the accompanying figures and detailed description which follow.

BRIEF DESCRIPTION OF THE DRAWINGS

FIG. 3B shows the signal in FIG. 3A provides a wide dynamic linear range.

FIG. 3D shows the signal in FIG. 3C provides a wide dynamic linear range.

FIGS. 9A-9B show Blots were washed in PBST and imaged on an Odyssey Fc in the 700 and 800 nm channels. FIG. 9B shows that β-Actin and α-Tubulin signals were unaffected by staining with SS2 as control (unstained) and test (stained).

FIGS. 10A-10D show proteins can be stained in a SDS-PAGE matrix.

FIGS. 11A-11D show results with compounds of the invention; proteins are visualize by visible light, which is detectable by the naked eye and fluorescent light.

DETAILED DESCRIPTION OF THE INVENTION

Figure 1A:
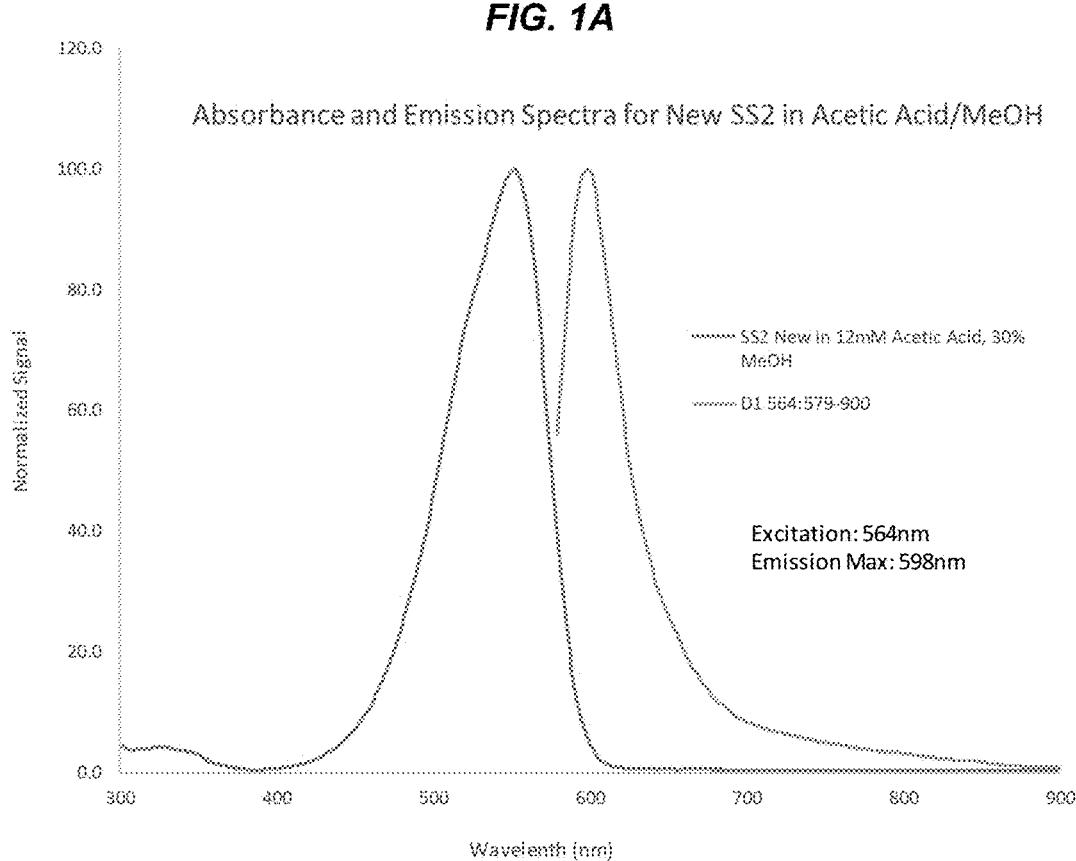
FIGS. 1A-1B show fluorescence spectra of a compound embodied in this disclosure.

The present disclosure embodies compounds, methods, and kits that are useful in connection with the detection of analytes of all types (e.g., biological molecules such as proteins, organic molecules, natural or synthetic molecules). The compounds of Formula I or I(a) are also referred to as dyes. The disclosure is particularly applicable to detection of proteins and nucleic acids using all types of membrane-based assays by techniques such as Western blotting, Dot blotting, Southern blotting, and Northern blotting. Furthermore, the present disclosure is applicable to the detection of analytes using all types of solution-based, luminometric assays, and immunological assays such as Cell based assays such as In-Cell Westerns, ELISAs (Enzyme Linked Immunoabsorbent Assays), bead assays, multiplex assays, tissue staining and the like.

I. Definitions

The terms "a," "an," or "the" as used herein not only include aspects with one member, but also include aspects with more than one member. For example, an embodiment of a method of imaging that comprises using a compound set forth herein would include an aspect in which the method comprises using two or more compounds set forth herein.

When the modifier "about" is applied to describe the beginning of a numerical range, it applies to both ends of the range. Thus, "from about 700 to 850 nm" is equivalent to "from about 700 nm to about 850 nm." When "about" is applied to describe the first value of a set of values, it applies to all values in that set. Thus, "about 680, 700, or 750 nm" is equivalent to "about 680 nm, about 700 nm, or about 750 nm." However, when the modifier "about" is applied to describe only the end of the range or only a later value in the set of values, it applies only to that value or that end of the range. Thus, the range "about 2 to 10" is the same as "about 2 to about 10," but the range "2 to about 10" is not.

"Activated acyl" as used herein includes a —C(O)-LG group. "Leaving group" or "LG" is a group that is susceptible to displacement by a nucleophilic acyl substitution (i.e., a nucleophilic addition to the carbonyl of —C(O)-LG, followed by elimination of the leaving group). Representative leaving groups include halo, cyano, azido, carboxylic acid derivatives such as t-butylcarboxy, and carbonate derivatives such as i-BuOC(O)O—. An activated acyl group may also be an activated ester as defined herein or a carboxylic acid activated by a carbodiimide to form an anhydride or mixed anhydride —OC(O)$R^a$ or —OC(N$R^a$)NH$R^b$, wherein $R^a$ and $R^b$ are members independently selected from the group consisting of $C_1$-$C_6$ alkyl, $C_1$-$C_6$ perfluoroalkyl, $C_1$-$C_6$ alkoxy, cyclohexyl, 3-dimethylaminopropyl, N-morpholinoethyl or aryl. Activated acyl groups include activated esters.

"Activated ester" as used herein includes a derivative of a carboxyl group that is more susceptible to displacement by nucleophilic addition and elimination than an ethyl ester group (e.g., an NHS ester, a sulfo-NHS ester, a PAM ester, or a halophenyl ester). Representative carbonyl substituents of activated esters include succinimidyloxy (—O$C_4H_4NO_2$), sulfosuccinimidyloxy (—O$C_4H_3NO_2SO_3H$), -1-oxybenzotriazolyl (—O$C_6H_4N_3$); 4-sulfo-2,3,5,6-tetrafluorophenyl; or an aryloxy group that is optionally substituted one or more times by electron-withdrawing substituents such as nitro, fluoro, chloro, cyano, trifluoromethyl, or combinations thereof (e.g., pentafluorophenyloxy). Activated esters include succinimidyloxy and sulfosuccinimidyloxy esters.

"Acyl" as used herein includes an alkanoyl, aroyl, heterocycloyl, or heteroaroyl group as defined herein. Representative acyl groups include acetyl, benzoyl, nicotinoyl, and the like.

"Alkyl" as used herein includes an aliphatic hydrocarbon group, which may be straight or branched-chain, having about 1 to about 20 carbon atoms in the chain. Alkyl groups have 1 to about 12 carbon atoms in the chain. Typically, alkyl groups have 1 to 10 or 1 to 6 carbon atoms in the chain. "Branched-chain" as used herein includes that one or more lower alkyl groups such as methyl, ethyl or propyl are attached to a linear alkyl chain (e.g., 2-methylbutyl). "Lower alkyl" as used herein includes 1 to about 6 carbon atoms, typically, 5 or 6 carbon atoms in the chain, which may be straight or branched. Representative alkyl groups include methyl, ethyl, n-propyl, isopropyl, n-butyl, t-butyl, n-pentyl, and 3-pentyl.

"Amino" as used herein includes a group of formula $Y_1Y_2N$— wherein $Y_1$ and $Y_2$ are independently hydrogen, acyl, aryl, or alkyl; or $Y_1$ and $Y_2$, together with the nitrogen through which $Y_1$ and $Y_2$ are linked, join to form a 4- to 7-membered azaheterocyclyl group (e.g., piperidinyl). Optionally, when $Y_1$ and $Y_2$ are independently hydrogen or alkyl, an additional substituent can be added to the nitrogen, making a quaternary ammonium ion. Representative amino groups include primary amino ($H_2N$—), methylamino, dimethylamino, diethylamino, tritylamino, and the like. Typically, "amino" is an —NRR' group where R and R' are members independently selected from the group consisting of H and alkyl. Typically, at least one of R and R' is H.

"Balanced charge" as used herein includes the condition that the net charge for a compound and its associated counterions be zero under standard physiological conditions. In order to achieve a balanced charge, a skilled person will understand that after the first additional sulfonato group that balances the +1 charge of the indolinium ring, a cationic counterion (e.g., the cation of a Group I metal such as sodium) must be added to balance the negative charge from additional sulfonato groups. Similarly, anionic counterions must be added to balance any additional cationic groups (e.g., most basic amino groups under physiological conditions). In some embodiments, a counterion can be covalently connected to the compound (e.g., a zwitterionic group containing a sulfonato-anionic group and a trialkylamino cationic group).

"Biomolecule" as used herein includes a natural or synthetic molecule for use in biological systems. Suitable biomolecules include a protein, a peptide, an enzyme substrate, a hormone, an antibody or a fragment thereof, an antigen, a hapten, an avidin, a streptavidin, a carbohydrate, a carbohydrate derivative, an oligosaccharide, a polysaccharide, a nucleic acid, a deoxynucleic acid, a fragment of DNA, a fragment of RNA, nucleotide triphosphates, acyclo terminator triphosphates, PNA, and the like.

As used herein, "protein" includes a polypeptide, or a sequence of two or more amino acids, which can be naturally-occurring or synthetic (modified amino acids, or amino acids not known in nature) linked by peptide bonds. As used herein, the term "protein" includes peptides.

A "detectable response" or "optical signal" as used herein includes a change in, or occurrence of, a parameter in a test system that is capable of being perceived, either by direct observation or instrumentally, and which is a function of the presence of a specifically targeted member in a sample. Such detectable responses include a change in, or appearance of, color, fluorescence, reflectance, pH, chemiluminescence, infrared spectra, magnetic properties, radioactivity, light scattering, x-ray scattering, or an electron-rich substrate. Appropriate labels to provide a detectable response include, but are not limited to, a compound of Formula I or I(a), a visible or fluorescent dye, an enzyme substrate that produces a visible or fluorescent precipitate upon enzyme action (for example, the action of horseradish peroxidase upon diaminobenzidine), visible or fluorescent labeled latex microparticles, or a signal that is released by the action of light upon the reagent (e.g. a caged fluorophore that is activated by photolysis, or the action of light upon diaminobenzidine).

A term "detectable" includes the presence of a material or the signal generated from the material is immediately detectable by observation, instrumentation, or film without requiring chemical modifications or additional substances.

A phrase "detectable by the naked eye" includes directly visible by a human being having normal vision without the aid of, for example, glasses that magnify or filter light or a microscope (or lens of any type that provides magnification), and without the aid of illumination of greater intensity than standard laboratory room fluorescent or incandescent lighting, or illumination with light of narrower wavelength(s) than standard laboratory room fluorescent or incandescent lighting, or illumination with wavelength(s) outside that of standard laboratory room fluorescent or incandescent lighting.

When any two substituent groups or any two instances of the same substituent group are "independently selected" from a list of alternatives, they may be the same or different. For example, if $R^a$ and $R^b$ are independently selected from the group consisting of methyl, hydroxymethyl, ethyl, hydroxyethyl, and propyl, then a molecule with two $R^a$ groups and two $R^b$ groups could have all groups be methyl.

Alternatively, the first $R^a$ could be methyl, the second $R^a$ could be ethyl, the first $R^b$ could be propyl, and the second $R^b$ could be hydroxymethyl (or any other substituents taken from the group). Alternatively, both $R^a$ and the first $R^b$ could be ethyl, while the second $R^b$ could be hydroxymethyl (i.e., some pairs of substituent groups may be the same, while other pairs may be different).

"Sulfonato" as used herein includes an $—SO_3^-$ group, balanced by a cation such as $H^+$, $Na^+$, $K^+$, and the like. Typically, the cation is non-toxic (e.g., a cation commonly used in pharmaceuticals). Representative cations include an alkali metal ion (e.g., sodium, potassium) or a tetraalkylammonium (e.g., tetraethylammonium), II. Compounds of Formula I and Formula I(a)

The present disclosure provides hemicyanine compounds or dyes having Formula I:

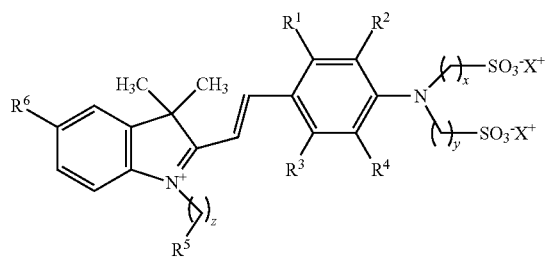

I wherein $R^1$, $R^2$, $R^3$, $R^4$, $R^5$ and $R^6$ are each a member independently selected from the group consisting of hydrogen, alkyl, alkenyl, halo, hydroxyl, alkoxy, amino, cyano, carboxyl, carboxylate, alkoxycarbonyl, amido, sulfonato, alkoxyalkyl, carboxyalkyl, alkoxycarbonylalkyl, sulfonatoalkyl, a functional group for conjugation to a biomolecule, and $R^7B$, wherein $R^7$ is the resultant attachment between the compound and a biomolecule after conjugation, wherein in Formula I, at least one of $R^1$, $R^2$, $R^3$, $R^4$, $R^5$ and $R^6$ is a functional group for conjugation or is $R^7B$;

B is a biomolecule;

x, y and z are each an integer independently selected from 1-10; and

X is hydrogen or a metal cation, wherein said compound has a balanced charge.

In certain aspects, $R^1$, $R^2$, $R^3$, $R^4$ and $R^5$ are each a member independently selected from hydrogen, alkyl, halo, hydroxyl, alkoxy, carboxyl, alkoxycarbonyl, amido, or sulfonate.

In certain aspects, $R^1$, $R^2$, $R^3$, $R^4$ and $R^5$ are each a member independently selected from hydrogen or alkyl.

In certain aspects, $R^6$ is a member selected from hydrogen, alkyl or sulfonate.

In certain aspects, x, y and z are each an integer independently selected from 3, 4, or 5.

In Formula I, at least one of $R^1$, $R^2$, $R^3$, $R^4$, $R^5$ and $R^6$ is a functional group for conjugation to a biomolecule or is $R^7B$, wherein $R^7$ is the resultant attachment between the compound of Formula I and a biomolecule after conjugation. In certain aspects, $R^5$ is a functional group for conjugation to a biomolecule. In certain aspects, $R^5$ is $R^7B$.

In certain aspects, the functional group for conjugation to a biomolecule is a member selected from the group of an amine, a carbamate, a carboxylic acid, a carboxylate, a maleimide, an activated acyl, an activated ester, N-hydroxysuccinimidyl, a hydrazine, a hydrazide, a hydrazone, an azide, an alkyne, an aldehyde, a thiol, and protected groups thereof for conjugation to a molecule or biomolecule.

In certain aspects, B is selected from a protein, a peptide, an enzyme substrate, a hormone, and an antibody or a fragment thereof.

In certain aspects, compounds or dyes embodied in this disclosure are in Table 1:

TABLE 1

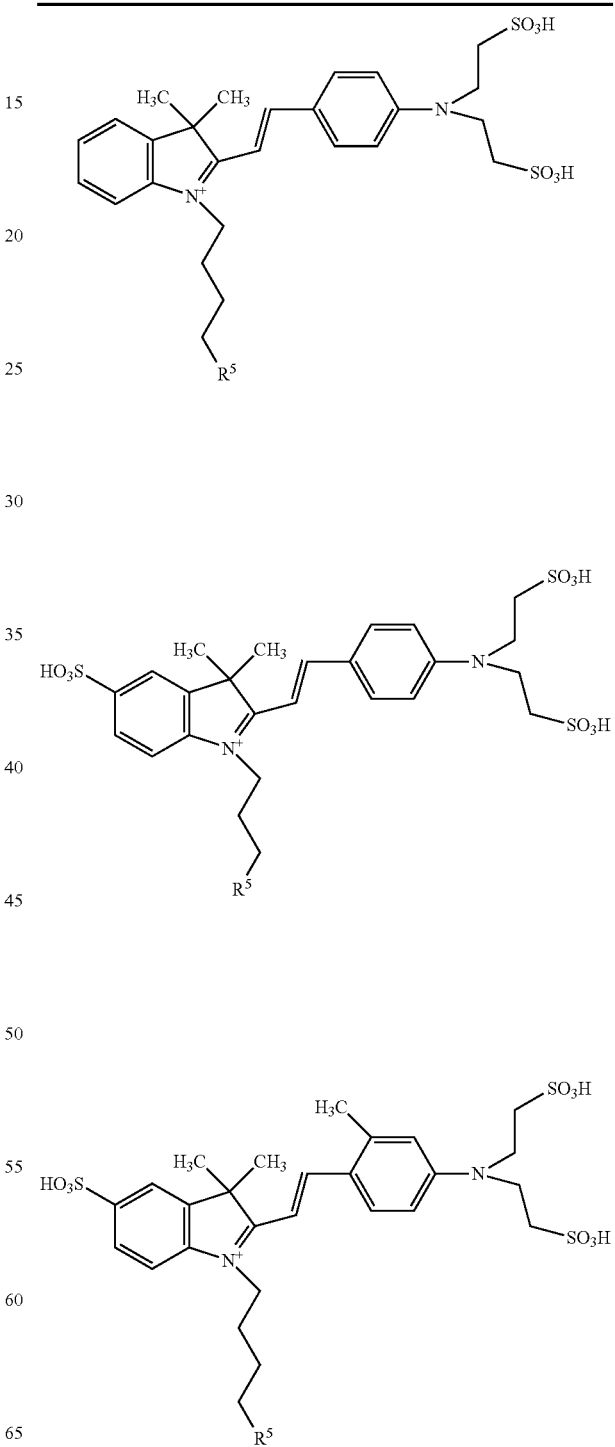

TABLE 1-continued

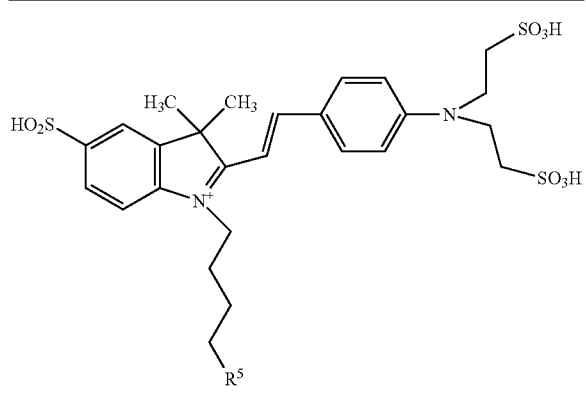

In certain aspects, $R^5$ is the functional group for conjugation to a biomolecule or is $R^7B$. For example, $R^5$ can be any of the functional groups set forth below. The wavy line is the attachment to the rest of the molecule.

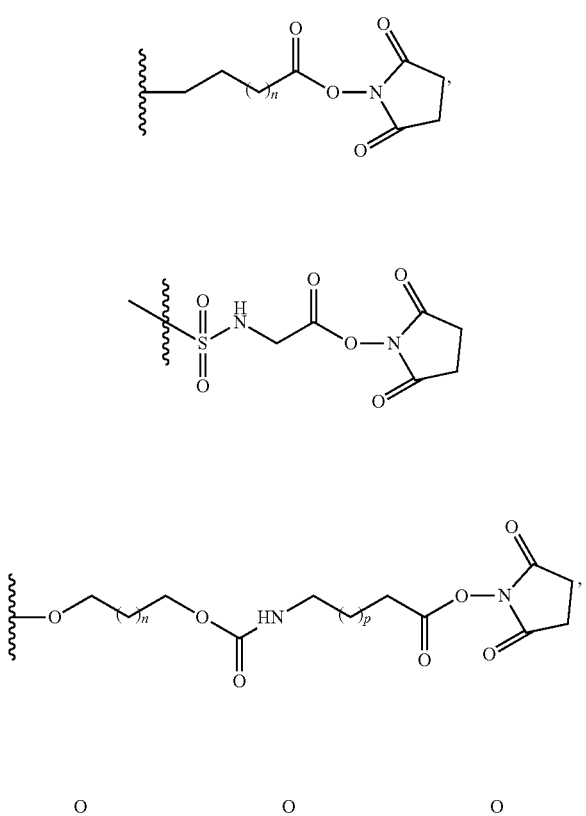

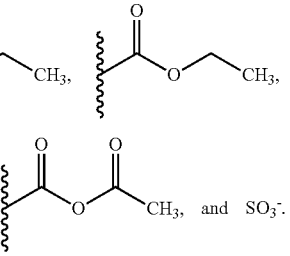

In another aspect, present disclosure provides hemicyanine compounds or dyes having Formula I(a):

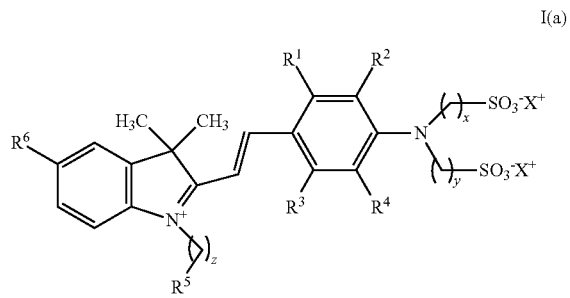

I(a)

wherein $R^1$, $R^2$, $R^3$, $R^4$, $R^5$ and $R^6$ are each a member independently selected from the group consisting of hydrogen, alkyl, alkenyl, halo, hydroxyl, alkoxy, amino, cyano, carboxyl, carboxylate, alkoxycarbonyl, amido, sulfonato, alkoxyalkyl, carboxyalkyl, alkoxycarbonylalkyl, x, y and z are each an integer independently selected from 1-10; and X is hydrogen or a metal cation, wherein said compound has a balanced charge.

In certain aspects, $R^1$, $R^2$, $R^3$, $R^4$ and $R^5$ are each a member independently selected from hydrogen, alkyl, halo, hydroxyl, alkoxy, carboxyl, alkoxycarbonyl, amido, or sulfonate.

In certain aspects, $R^1$, $R^2$, $R^3$, $R^4$ and $R^5$ are each a member independently selected from hydrogen or alkyl.

In certain aspects, $R^6$ is a member selected from hydrogen, alkyl or sulfonate.

In certain aspects, x, y and z are each an integer independently selected from 3, 4, or 5.

In certain aspects, compounds or dyes embodied in this disclosure are in Table 1A:

TABLE 1A

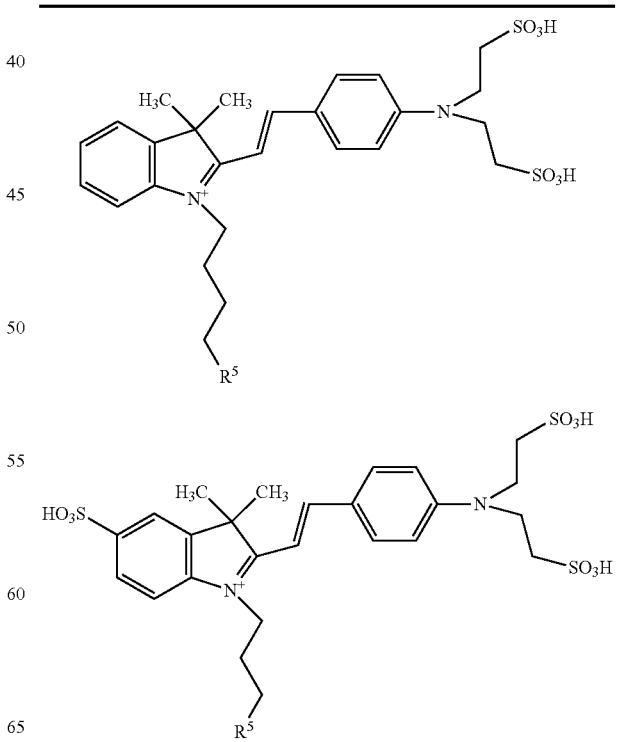

TABLE 1A-continued

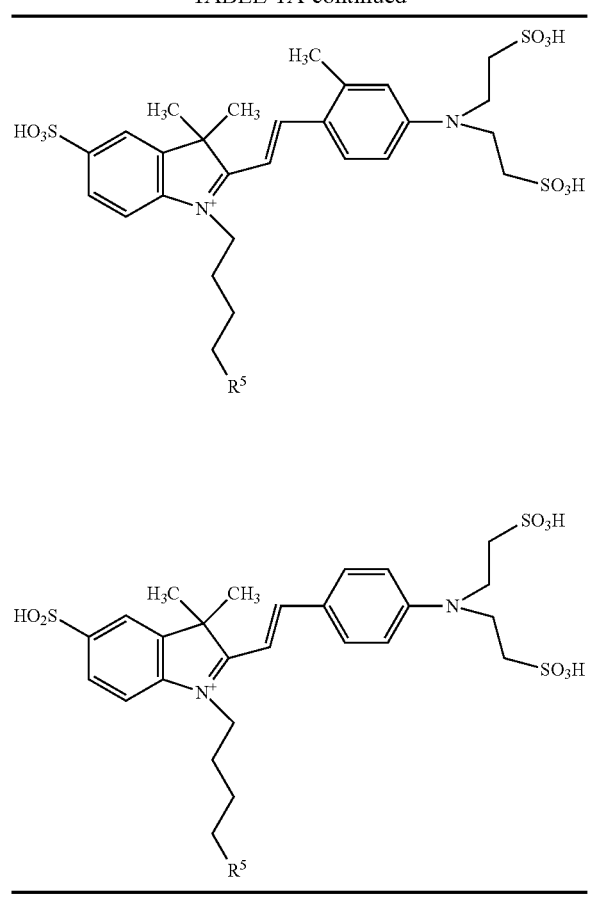

In certain aspects, $R^5$ in the above compounds is a sulfonate group.

III. Methods of Making Compounds of Formula I or I(a)

Scheme I

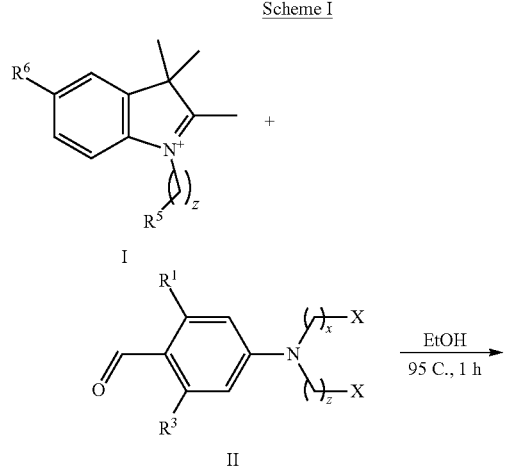

The compounds of Formula I or I(a) can be made by a variety of methods. Scheme I illustrates an exemplary method and is not intended to be limiting. In brief, to a stirred solution of a substituted indole, an alkanol is added with an aniline II in slight excess and the mixture is heated a about 85-105° C. to yield the hemicyanine intermediate III.

The reaction mixture is cooled and the reaction solution is concentrated under reduced pressure. A solution of $Na_2SO_3$ in water is added and the mixture is heated. Afterwards, acid is added until an acidic pH is reached and then the reaction is heated.

Solvents are then concentrated under reduced pressure and the crude reaction is purified by reverse phase column chromatography to yield product IV as a free acid and then passed through a short pad of Amberlite IR-120 Resin to yield the final product IV as the sodium salt.

In an alternative synthetic route shown in Scheme II below, a suspension of I (10.15 mmol, 1.0 equiv) in water (10 mL) is added $Na_2SO_3$ (22.35 mmol, 2.2 equiv) and the reaction is refluxed overnight. The mixture can then be cooled and product precipitated with ethanol. The solid is re-dissolved in 2M HCl, re-precipitated with ethanol and dried (vacuum oven) for 1 hour.

Dry intermediate II (7.4 mmol, 1.0 equiv), compound III (7.4 mmol, 1.0 equiv) and sodium acetate (37.1 mmol, 5.0 equiv) are dissolved in water and the mixture is stirred at 80° C. for 1 hour. The mixture is then cooled to room temperature and final product SS2 is obtained by precipitation with ethanol.

Scheme II

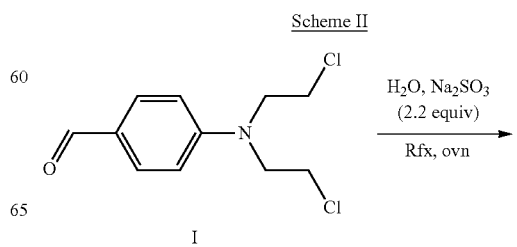

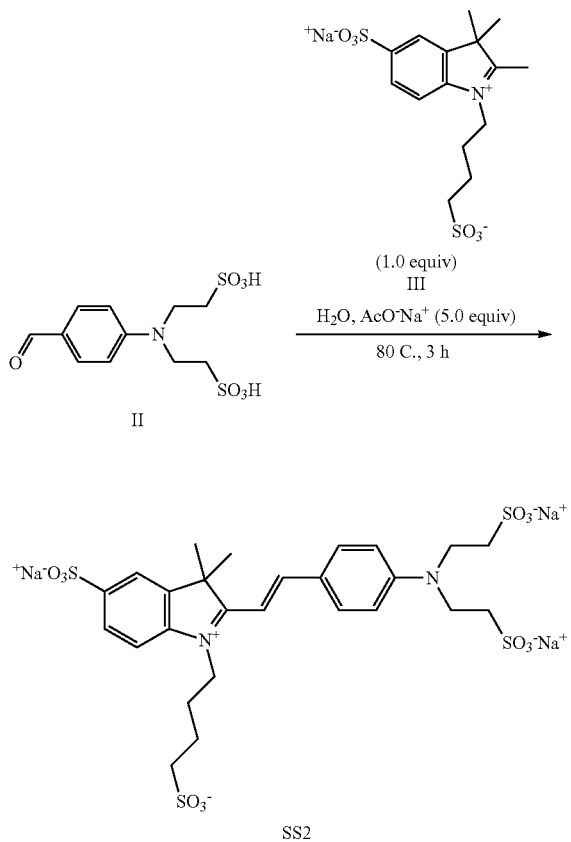

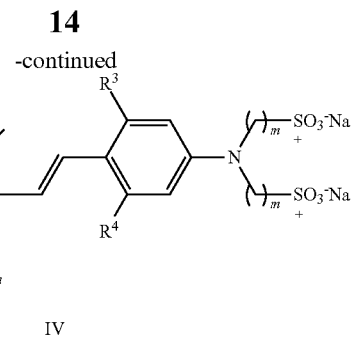

IV. Bioconjugates of Formula I

Other compounds of Formula I or Formula I(a) can be made using the appropriate substituted aniline (I) as shown in Scheme III.

Scheme III

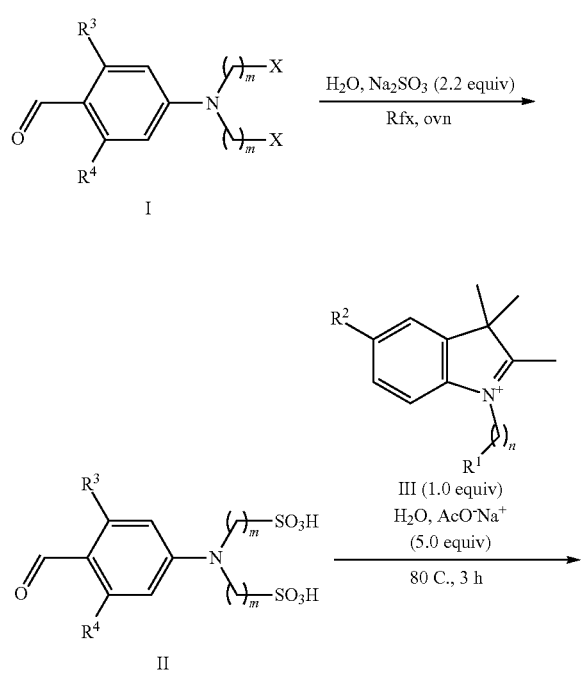

In certain aspects, the disclosure embodies a method or process for labeling a ligand or biomolecule with a compound or dye of Formula I, the method comprising: contacting a ligand or biomolecule with a compound having Formula I to generate the corresponding bioconjugate. In certain aspects, compounds of Formula I are conjugatable or have been conjugated to a biomolecule.

In one aspect, $R^5$ is a functional group that reacts with a thiol, a hydroxyl, a carboxyl, or an amino group on a biomolecule, forming a linking group between the dye of Formula I and the biomolecule ($R^7B$). In certain aspects, this reaction is carried out in mixtures of aqueous buffer and an organic solvent such as DMF at pH 8 to 9. Alternatively, this reaction is carried out in distilled water or in an aqueous buffer solution. For thiols or for acidic groups, a pH of 7 or lower is typical for the reaction solvent, especially if a substrate also contains a reactive amino group.

Selected examples of reactive functionalities (i.e., wherein at least one of $R^1$, $R^2$, $R^3$, $R^4$, $R^5$ or $R^6$ is a functional group for conjugation) useful for attaching a compound of Formula I to a ligand or biomolecule are activated acyl groups, activated esters, acyl halides, anhydrides, carbodiimides, epoxides, maleimides, and isocyanates.

Dyes can include reactive functionalities, such as cysteine reactive groups (e.g., maleimide, iodoacetic acid, iodoacetamide, and vinyl sulfone) or amino reactive groups (such as, for example, isothiocyanates, isocyanates, acyl azides, N-hydroxysuccinimide (NHS) esters, sulfonyl chlorides, aldehydes, ketones, glyoxals, epoxides, oxiranes, carbonates, aryl halides, imidoesters, carbodiimides, and acid anhydrides). Reactive chemical groups such as, for example, a N-hydroxysuccinimide (NHS) can be added to a dye using techniques that are known in the art of organic chemistry.

Column A of Table 2 is a list of the reactive functionalities, which can be on the compound of Formula I or a biomolecule. Column B is a list of the complementary reactive groups (e.g., a carboxyl, hydroxyl, thiol, or amino functionality), which can be on the biomolecule or the compound of Formula I and reacts with the indicated functionality of Column A to form the bond of Column C (e.g., $R^7B$). In other words, $R^7B$ is the resultant bond after a compound of Formula I reacts with a biomolecule, i.e., the conjugate comprises $R^7B$. In certain aspects, at least one of $R^1$, $R^2$, $R^3$, $R^4$, $R^5$ and $R^6$ is $R^7B$. Those of skill in the art will know of other bonds suitable for use in the present disclosure.

TABLE 2

Exemplary Bonds for Linking Groups

| A<br>Reactive Functionality<br>(Compound of Formula I<br>or Biomolecule, a<br>functional group for<br>conjugation) | B<br>Complementary Group<br>(Biomolecule or<br>Compound of Formula I) | C<br>Resulting Linking Group<br>($R^7B$) |
|---|---|---|
| activated esters* | amines/anilines | amides |
| acrylamides | thiols | thioethers |
| acyl azides** | amines/anilines | amides |
| acyl halides | amines/anilines | amides |
| acyl halides | alcohols/phenols | esters |
| acyl nitriles | alcohols/phenols | esters |
| acyl nitriles | amines/anilines | amides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| anhydrides | alcohols/phenols | esters |
| anhydrides | amines/anilines | amides/imides |
| aryl halides | thiols | thiophenols |
| aryl halides | amines | aryl amines |
| azides | Alkynes | 1,2,3-triazoles |
| azides | ester with phosphine reagent (e.g., o-diphenylphosphino group) | amide (and phosphine oxide) |
| aziridines | thiols | thioethers |
| boronates | glycols | boronate esters |
| boronates/boronic acids | aryl halides | C-C bond to aryl ring |
| boronates/boronic acids | alkenyl halides | C-C bond to alkenyl group |
| activated carboxylic acids | amines/anilines | amides |
| activated carboxylic acids | alcohols | esters |
| activated carboxylic acids | hydrazines | hydrazides |
| carbodiimides | carboxylic acids | N-acylureas or anhydrides |
| diazoalkanes | carboxylic acids | esters |
| electron-rich diene | dienophile (e.g., electron-poor alkene) | cyclohexene (Diels-Alder cycloaddition) |
| epoxides | thiols | thioethers |
| epoxides | amines | alkyl amines |
| epoxides | carboxylic acids | esters |
| haloacetamides | thiols | thioethers |
| haloplatinate | amino | platinum complex |
| haloplatinate | heterocycle | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| photoactivatable group | varies; see definition | varies; see definition |
| quadricyclanes | electrophile (e.g., Ni bis(dithiolene)) | norbornene cycloaddition product |
| silyl halides | alcohols | silyl ethers |
| sulfonyl azides | thiocarboxylic acids | N-acyl sulfonamides |
| sulfonate esters | amines/anilines | alkyl amines |
| sulfonate esters | carboxylic acids | esters |
| sulfonate esters | thiols | thioethers |
| sulfonate esters | alcohols/phenols | ethers |
| sulfonyl halides | amines/anilines | sulfonamides |
| 1,2,4,5-tetrazine | alkene | dihydropyradazine |
| vinyl sulfonyl | thiols | thioethers |
| vinyl sulfonyl | activated diene | cyclohexenyl (Diels-Alder) |

*Activated esters, as understood in the art, generally have the formula —C(O)OM, where —OM is a leaving group (e.g. succinimidyloxy (—$OC_4H_4NO_2$), sulfosuccinimidyloxy (—$OC_4H_3NO_2SO_3H$), -1-oxybenzotriazolyl (—$OC_6H_4N_3$); 4-sulfo-2,3,5,6-tetrafluorophenyl; or an aryloxy group or aryloxy substituted one or more times by electron withdrawing substituents such as nitro, fluoro, chloro, cyano, or trifluoromethyl, or combinations thereof, used to form activated aryl esters; or —C(O)OM is a carboxylic acid activated by a carbodiimide to form an anhydride or mixed anhydride —C(O)OC(O)$R^a$ or —C(O)OC(N$R^a$)NH$R^b$, wherein $R^a$ and $R^b$ are members independently selected from the group consisting of $C_1$-$C_6$ alkyl, $C_1$-$C_6$ perfluoroalkyl, $C_1$-$C_6$ alkoxy, cyclohexyl, 3-dimethylaminopropyl, or N-morpholinoethyl).
**Acyl azides can also rearrange to isocyanates.

When linking a compound of Formula I having a carboxylic acid with an amine-containing ligand or biomolecule, the carboxylic acid can first be converted to a more reactive form, e.g, a N-hydroxy succinimide (NHS) ester or a mixed anhydride, by means of an activating reagent. The amine-containing ligand or biomolecule is treated with the resulting activated acyl to form an amide linkage. This reaction is carried out in aqueous buffer at pH 8 to 9 with DMSO or DMF as an optional co-solvent. Alternatively, this reaction is carried out in distilled water or in an aqueous buffer solution.

The attachment of an isocyanate- or isothiocyanate-containing compound of Formula I is analogous to the procedure for the carboxy dye, but no activation step is required. The amine-containing ligand or biomolecule is treated directly with the activated acyl compound to form a urea or a thiourea linkage. In certain aspects, the reaction is carried out in aqueous buffer at pH 9 to 10 with DMSO or DMF as an optional co-solvent. Alternatively, this reaction is carried out in distilled water or in an aqueous buffer solution.

In one aspect, the biomolecule is a protein such as an antibody. In one example, antibody labeling is carried out in a buffer optionally including an organic co-solvent, under basic pH conditions, and at room temperature. In certain aspects, the labeled antibody is purified by dialysis or by gel permeation chromatography using equipment such as a SEPHADEX® G-50 column to remove any unconjugated compound of Formula I. Those of skill in the art will know of other ways and means for purification.

In another aspect, the biomolecule contains a thiol group that forms the linking group by reaction with for example, a maleimidyl substituent at $R^5$. In certain aspects, the biomolecule is a protein, a peptide, an antibody, a thiolated nucleotide, or a thiolated deoxynucleotide.

If the compound of Formula I or biomolecule has a reactive hydroxyl group, it can be linked to a ligand or biomolecule by means of phosphoramidite chemistry, which ultimately forms a phosphate linkage between the dye and the biomolecule. For examples of such labeling methods, see U.S. Pat. No. 6,027,709, which discloses many linking groups, linking methods, and biomolecules that can be readily labeled. In one embodiment, solid-phase synthesis is disclosed in U.S. Pat. No. 6,027,709.

In another aspect, the biomolecule is DNA or RNA. Use of phosphoramidite chemistry allows labeling of a DNA or an RNA during the synthesis process. The protected nucleotide is labeled while attached to a solid-phase support. The free 5'-OH group is reacted with the phosphoramidite and a tetrazole activator to form a phosphite linkage which subsequently is oxidized to phosphate. The labeled DNA or RNA is then cleaved from the solid phase by means of ammonia or by another standard procedure.

V. Methods Using Compounds of Formula I and Formula I(a)

In another embodiment, the disclosure embodies an assay method for measuring an analyte in a sample, the method comprising:
a) contacting the sample with a binding agent that binds to an analyte to form an analyte complex;
b) contacting the sample with a compound or dye of Formula I or I(a), wherein the compound of Formula I or I(a) reacts with the analyte complex to form a detectable agent; and
c) upon excitation, detecting an optical signal from the detectable agent. The optical signal can be fluorescence.

In one aspect, the assay method is an immunological detection method. Suitable immunological detection methods include, but are not limited to, an enzyme linked immunosorbent assay (ELISA), a Western blot analysis, and an immunohistochemical analysis.

In one aspect, the disclosure embodies compounds, methods and kits for a total protein stain having a detectable response at 520-600 nm such as for example, 520, 530, 540, 550, 560, 570, 580, 590, or 600 nm, for use in for example, a Western Blot.

In certain aspect, the absorbance of a compound of Formula I or I(a) is at about 550 nm and the emission or optical signal is at about 570 nm. In certain instances, a dye can be, for example, a chromophore, a fluorophore or both a chromophore and a fluorophore. A fluorophore can be excited by visible light even ambient light or non-visible light (for example, UV light). A "chromophore" is a chemical group or compound capable of selective light absorption resulting in the coloration of the organic compound. In one aspect, the dyes of the disclosure are excited under ambient light and appear with color such as they appear pink.

In certain aspects, the compounds or dyes are able to detect biomolecules on Western Blot and ELISA by fluorescence. The fluorogenic detection method gives good sensitivity. In certain aspects, the compounds and methods give sensitivity enhancement as compared to chromogenic substrates.

In certain instances, the compounds, methods and kits embodied herein are used in Enzyme Linked Immunosorbent Assays (ELISAs), which utilize an enzyme label for the detection of proteins. Typically, a specific antibody is passively absorbed to a plate. The nonspecific sites are blocked with a protein solution which has no active part in the specific immunochemical reaction of a particular assay. A specific protein of interest is captured by the antibody on the surface and then detected by another antibody (a secondary antibody) with a compound of Formula I or I(a) as a label. The fluorescent label of Formula I or I(a) is conjugated to the secondary antibody and detected.

In a Western Blot application, a protein(s) is detected by first separating protein samples electrophoretically on for example, a SDS polyacrylamide gel. The proteins are then transferred electrophoretically to a membrane such as nitrocellulose or PVDF. The nonspecific sites are blocked with a protein solution that has no active part in the specific immunochemical reaction of a particular assay. A specific protein of interest is detected then by the addition of an antibody made against the protein. After a wash step to remove any unbound antibody, an antibody labeled with a compound or dye of Formula I or I(a) is added that will react with the primary antibody. The unbound labeled antibody is removed by a series of wash steps. The membrane is then exposed to an excitation light source to image or detect the near infrared fluorescence.

Typically, the proteins and peptides in the sample mixture have a molecular weight greater than about 500 daltons. More typically, the proteins and peptides are more than 800 daltons. Smaller polymers of amino acids (in the <1000 dalton range) are generally difficult to separate from the detergent front on denaturing gels, and typically do not adhere to filter membranes, but are still readily detected in solution. There is no precise upper limit on the size of proteins that may be stained and detected, except that they can not be so bulky that they precipitate out of solution. In one embodiment, the peptides and proteins are a mixture of different molecular weights that are used as molecular weight standards.

Where the sample mixture is an aqueous solution, the peptides and proteins of the sample mixture are typically present in a concentration of about 10 ng/mL-50 µg/mL, or in a concentration of 30 ng/mL-10 µg/mL, or in a concentration of 50 ng/mL-5 µg/mL. Where the sample mixture is an electrophoretic gel, the proteins or peptides of the sample mixture are typically present in a concentration of 1 ng/band-4 µg/band.

To make a staining mixture to combine with the sample mixture, the selected dye of Formula I or I(a) is typically first dissolved in an organic solvent, such as methanol, DMSO, DMF or short chain alkanols, usually to a dye concentration of 1-10 mM. This concentrated stock solution is then generally diluted with an aqueous solution according to the assay being performed. Staining solutions can be stored and reused for months without signal loss. Acetic acid is optionally included in the staining mixture, typically to a concentration of 5%-7.5% acetic acid, e.g. to improve labeling of gels relative to that obtained for dyes in water. For staining polypeptides in solution, the dye is diluted into an aqueous solution, preferably a buffered solution, that optionally contains a detergent. For staining proteins on gels or membranes, the dyes are diluted into water or buffer.

For visible color detection, dye concentrations in the staining mixture are typically between 1 µM and 100 µM, or between about 5 µM and about 20 µM; or at least 10-15 µM or higher, although concentrations below or above these values also results in detectable staining for certain proteins. Visible color is detectable by the naked eye and by ambient light.

For fluorescence detection, dye concentrations are typically greater than 0.10 µM and less than 10 µM; or greater than about 0.50 µM and less than or equal to about 5 µM; or 1-3 µM. Although concentrations below and above these values likewise result in detectable staining for certain samples, depending on the sensitivity of the detection method, dye concentrations greater than about 10 µM generally lead to quenching of the fluorescence signal. The sensitivity for visible color detection is generally lower than that observed with fluorescence detection. Visible color is detecatble by the naked eye.

A particular compound or dye of Formula I or I(a) is generally selected for a particular assay using one or more of the following criteria: sensitivity to a protein, dynamic range, photostability, staining time, and insensitivity to the presence of nucleic acids. The dyes disclosed herein have a sensitivity of 1-2 ng or less of protein per band in electrophoretic gels, or 10-30 ng or less of protein per mL of solution.

In certain aspects, a compound or dye of Formula I or I(a) is used to qualitatively and/or quantiatively stain proteins on SDS-PAGE and tricine gels. In addition, compounds of the disclosure can quantitatively and/or qualitatively stain proteins on nitrocellulose and PVDF membranes for western blots.

In certain aspects, a substrate, support or matrix is used with the methods described herein. Suitable substrates include, but are not limited to, filter paper, cellophane, cellulose acetate, nitrocellulose, nylon, poly(vinylidene difluoride) (PVDF), combinations thereof, and the like.

In certain aspects, the sample is present on or in a solid or semi-solid matrix. In one embodiment, the solid or semi-solid matrix comprises a membrane, such as a filter membrane. In another embodiment, the solid or semi-solid matrix comprises an electrophoresis medium, such as a polyacrylamide gel, agarose gel, linear polyacrylamide solution, polyvinyl alcohol gel, or capillary electrophoresis buffer. In one aspect, the solid or semi-solid matrix comprises a membrane, such as a nitrocellulose or poly(vinylidene difluoride) membrane, wherein the poly(amino acids) are immobilized on the membrane by blotting, spotting, or other method of application. In other embodiments, the solid or semi-solid matrix can be a SDS-PAGE gel.

In certain aspects of the present disclosure, the electrophoretic medium is a gel matrix. The gel matrix is a 1D- or 2D-gel. Suitable 1D- or 2D-gels include, but are not limited to, agarose gels, modified agarose gels, immobilized pH gradient gels, isoelectric focusing gels, polyacrylamide gels, polyvinyl alcohol gels, SDS-PAGE gels, starch gels, denaturing gels, non-denaturing gels, combinations thereof, and the like. Suitable polyacrylamide gels include, for example, Tris-glycine gels, Tris-tricine gels, mini- or full-size gels, and the like. In some embodiments, separated proteins or polypeptides in electrophoretic gels are post-stained using the staining mixture, or are transferred to a filter membrane or blot or other solid or semi-solid matrix before being combined with the staining mixture.

In another aspect, the electrophoretic medium may be a gel matrix having a film or polymer backing, such as the precast polyacrylamide gels having a film backing or precast polyacrylamide gels having a polyester backing.

In another aspect, the substrate or support can be a tissue slide or microscope slide for immunohistochemical (IHC) applications or imaging. The tissue samples may be prepared before the staining can be performed. The tissue slides may be subjected to a pretreatment process depending on the type of staining process that may be performed on the tissue. This pretreatment could include a deparafinization or a target retrieval. The preparation of the tissues on the slides may often be carried out manually in the laboratory. This pretreatment may include immersing the slide in a buffer or other types of processing liquid for a predetermined amount of time and temperature. Sample processing in immunohistochemical (IHC) applications and in other chemical and biological analyses may require one or a number of various processing sequences or protocols as part of an analysis of one or more samples.

In certain aspects, a compound or dye of Formula I or I(a) can be used to conjugate biomolecules and polymeric materials using a variety of dye modifications/functionalizations.

In certain aspects, the stain binds proteins by establishing both hydrophobic and ionic interactions within a specific pH range. Upon binding, all proteins in the sample can be measured by fluorescence intensity ($\lambda_{em}$ ~600 nm) for both qualitative and quantitative applications.

In certain aspects, a dye can be used as a total protein stain to detect the total protein in each lane of any gel or blot. Total protein staining is a direct measure of the total amount of sample protein in each lane. For each lane, the sum of all the signal intensities of all the proteins in the lane is used for normalization. The total protein stain produces a linear increase in signal intensity in response to increasing protein concentration. Signal intensity can be used to correct for variation at all points in the Western blot process, including gel loading and transfer to a membrane. Use of the stain is compatible with downstream immunodetection processes. Total protein stain provides linear, proportional signal across a broad range of sample concentrations.

In yet another embodiment, the present disclosure provides a method for performing protein analysis by electrophoresis, the method comprising:

(a) electrophoresing a plurality of proteins to form a separated protein mixture;
(b) transferring the separated protein mixture to a membrane;
(c) adding a compound of Formula I or I(a) to form an optical response such as a fluorescent signal; and
(e) capturing the fluorescent signal with a film or an imager.

In certain aspects, the electrophoresis is in a gel, such as polyacrylamide. A SDS-PAGE method comprises gel preparation, sample preparation, electrophoresis, protein staining or western blotting and analysis of the generated banding pattern.

In certain aspects, during sample preparation, a sample buffer and SDS are added to the proteins, and the sample is heated to about 95° C. for five minutes to disrupt secondary and tertiary structures by disrupting hydrogen bonds and stretching the molecules. Optionally, disulfide bridges can be cleaved by reduction. In addition to the samples, a molecular-weight size marker (protein ladder) is usually loaded onto the gel. This are proteins of known sizes and thereby allows the estimation of the sizes of the proteins in the actual samples, which migrate in parallel in different tracks or lanes of the gel. The size marker is often pipetted into the first or last pocket of a gel.

In some instances, the protein standard is included with the test sample and run on a SDS-PAGE polyacrylamide gel, e.g., NuPAGE® Bis-Tris gel with 1× NuPAGE® MES-SDS Running Buffer (Thermo Fisher Scientific, Waltham, Mass.) at 160V, constant voltage for about 55 minutes. The proteins can be stained and analyzed using a digital imaging system equipped with fluorescence detectors. Alternatively, the SDS-PAGE gel can undergo western blotting processing. The proteins can be transferred to a membrane, e.g., a nitrocellulose, PVDF or the like membrane).

In some aspects, the membrane is nitrocellulose or PVDF. In some aspects, a the protein standard is loaded with an unknown protein.

In some aspects, the denatured samples are loaded onto a gel of polyacrylamide, which is placed in an electrophoresis buffer with suitable electrolytes. Thereafter, a voltage (usually around 100 V, 10-20 V per cm gel length) is applied, which causes a migration of negatively charged molecules through the gel in the direction of the anode. The fastest-migrating proteins (with a molecular weight of less than 5 KDa) form the buffer front together with the anionic components of the electrophoresis buffer, which also migrate through the gel.

In some aspects, at the end of the electrophoretic separation, all proteins are sorted by size and can then be analyzed by other methods, e.g. protein staining or immunological detection such as the Western Blot using a compound of Formula I or I(a).

In a Dot Blot, proteins are directly applied to a membrane and detected with an antibody system as described.

In a Southern blot, DNA is detected by first separating the DNA sample electrophoretically on an agarose gel. The DNA is then transferred to a membrane such as charge-modified nylon. The DNA is then fixed by irradiation or baking. The membrane is then blocked with a prehybridization buffer to prevent any nonspecific binding of a DNA probe. The DNA probe coupled to a detectable label such as biotin is then added to the membrane and is allowed to incubate for several hours at 50° C. or higher. The blots then undergo a series of stringency washes to remove any non-specific hybridized probe from the DNA target while maximizing target/probe interactions. The blots are blocked again to prevent any nonspecific binding of the enzyme labeled probe. A labeled conjugate such as streptavidin labeled with a compound of Formula I or I(a) is added to the membrane. The membrane is washed to remove any unbound label. The membrane is then exposed to an excitation light source to image or detect the near infrared fluorescence.

In yet another embodiment, the disclosure embodies a method for detecting an analyte in a sample, said method comprising:
a) combining the sample and a compound of Formula I or I(a),
b) exciting the sample with light; and
c) detecting an optical signal such as fluorescence from the a compound of Formula I or I(a), thereby detecting the analyte.

In one embodiment, the disclosure provides a method for staining and or detecting a protein, the method comprising:
contacting a staining mixture that contains a compound or dye of Formula I or I(a) with a protein to form a combined mixture;
incubating the combined mixture for a time sufficient for the compound or dye of Formula I or I(a) to associate with the protein to form a dye complex that gives an optical response upon illumination;
illuminating the dye-protein complex; and
detecting the optical response.

In some aspects, the dye complex association is reversible. Typically, the dye complex association is performed at an acidic pH. The acidic pH can be in a range of 1 to 6; or in a range of 3 to 5 or stain proteins at low pH (e.g., 3-5, such as 3, 4, or 5).

In some aspects, the dye complex disassociation or reversibility is performed at a basic pH. The such as in a range of high pH or 8 to 14, or in a range of 8 to 11 (e.g., 8-11 such as 8, 9, 10 or 11).

In some aspects, the dye complex association is a covalent complex.

Various reversal solutions include for example, carbonate buffer at pH 9.0-10; sodium hydroxide at pH >10 and sodium hydroxide and methanol.

In still yet another embodiment, the disclosure embodies a method for detecting a target biomolecule in a sample, the method comprising:
a) providing a sample that is suspected of containing a target analyte;
b) providing a compound of Formula I or I(a) conjugated to a capture molecule, wherein the capture molecule is capable of interacting with the target analyte;
c) contacting the sample with the capture molecule and the compound of Formula I or I(a) under conditions in which the capture molecule can bind to the target analyte if present;
d) applying a light source to the sample that excites the compound of Formula I or I(a); and detecting whether light or optical signal is emitted from the conjugated compound of Formula I or I(a).

In certain instances, the capture molecule is an antibody.

In certain instances, their emission wavelengths is in the NIR spectrum, between 550-850 nm or about 600-825 nm or about 650 and 800 nm. After excitation, the near infared fluoresence emission and intensity of the the oxidized substrate can be detected using a fluorometer or fluorescence imager. Suitable systems for detection include the LI-COR Odyssey Systems including Odyssey CLx, Odyssey Sa and Odyssey Fc. In addition to the foregoing, a plate reader or spectrophotometer can be used and the amount of absorbance can be measured.

VI. Kits

The disclosure provides kits. In one embodiment, the disclosure provides a kit for staining a protein in a sample, the kit comprising:

a) a compound or dye or Formula I or I(a); and b) instructions for combining the compound of Formula I or I(a) with a sample containing or thought to contain protein; the instructions comprising:

i) combining a sample that is thought to contain a protein with a staining mixture that contains the compound of Formula I or I(a) to form a combined mixture; and ii) incubating the combined mixture for a time sufficient for the dye in the staining mixture to associate with the protein in the sample mixture to form a dye-protein complex that gives a detectable optical response upon illumination.

In one aspect, instructions further specify subjecting the sample to electrophoresis before, during or after being combined with the dye.

In some embodiments, the kit includes assay components, e.g., for running an ELISA, or Western blot and instructions for use. A Western Blot kit can include, in addition to at least one container of a compound of Formula I or I(a), appropriate membranes, separation components (e.g., agarose or SDS/PAGE gels), solutions, and reagents for carrying out the immunoassay. In some embodiments, the Western Blot kit can include containers with antibodies, optionally with positive and negative control samples. In some embodiments, the user will provide the desired test sample and/or the target-specific antibody to be labeled.

In some embodiments, the kit also includes components for immunoprecipitation, e.g., beads or other matrix associated with a capture agent. For example, the matrix can be coated with a substance that has affinity for proteins, for a particular tag (e.g., Ni resin, streptavidin, etc.), or nucleotides generally.

In some embodiments, the kit can provides a compound of Formula I or I(a) for conjugation to a desired antibody. The kit can also include disposable labware, e.g., for injection or other administration.

The current compounds and methods possess many advantages over known methods for staining proteins on gels. For example, staining is very rapid, and is relatively insensitive to protein composition. Visualization of stained gels is possible without destaining, and the stained bands remain readily detectable for several days. The dyes used in the current method are readily soluble and stable in aqueous staining solutions. In addition, the dyes exhibit a large Stokes shift between the absorbance and emission maxima. Finally, the staining procedure of the present disclosure is rapid and simple, requires minimal labor, and allows the detection of as little as 1 ng of protein per band.

The current compounds and methods can also be used to detect proteins on filter membranes or other solid supports, or in solution. The use of the dyes of the current disclosure for staining proteins in solution can be used to quantitate proteins with high sensitivity.

EXAMPLES

Example 1 illustrates a synthetic procedure for a compound of the present disclosure.

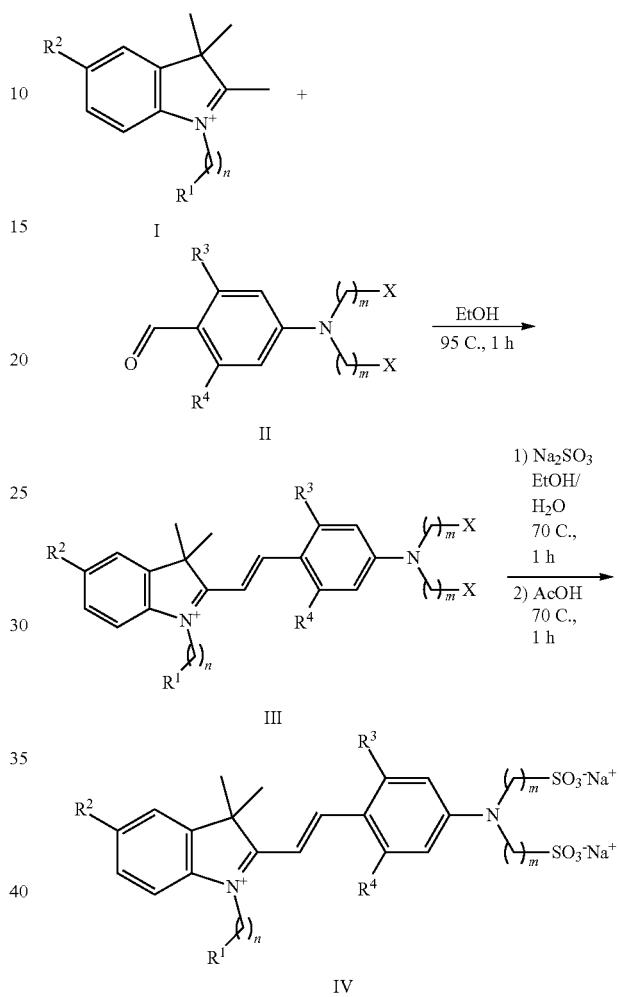

To a stirred solution of I (0.30 mmol, 1.0 equiv) in 15 mL EtOH was added II (0.33 mmol, 1.1 equiv) and the mixture was heated at 95° C. for 1 h to yield the formation of intermediate III. The reaction mixture was then cooled down, and EtOH was concentrated under reduced pressure, until ~5 mL were left. A solution of Na$_2$SO$_3$ (6.0 mmol, 20 equiv) in 20 mL H$_2$O was then added, and the mixture heated at 70° C. for 1 h. Afterwards, AcOH was added until acidic pH and the reaction was heated for 1 additional hour. Solvents were concentrated under reduced pressure until ~10 mL were left and reaction crude was purified by reverse phase column chromatography using H$_2$O/CH$_3$CN+0.5% TFA to yield product IV as free acid. Fractions containing the product were combined and solvents evaporated. The resulting material was dissolved in water and passed through a short pad of Amberlite IR-120 Resin to yield the final product IV as the sodium salt.

Example 2 illustrates representative compounds of the present disclosure.

Using the procedure outlined in Example 1, but varying the reactants, Compounds SS1-SS4 were made.

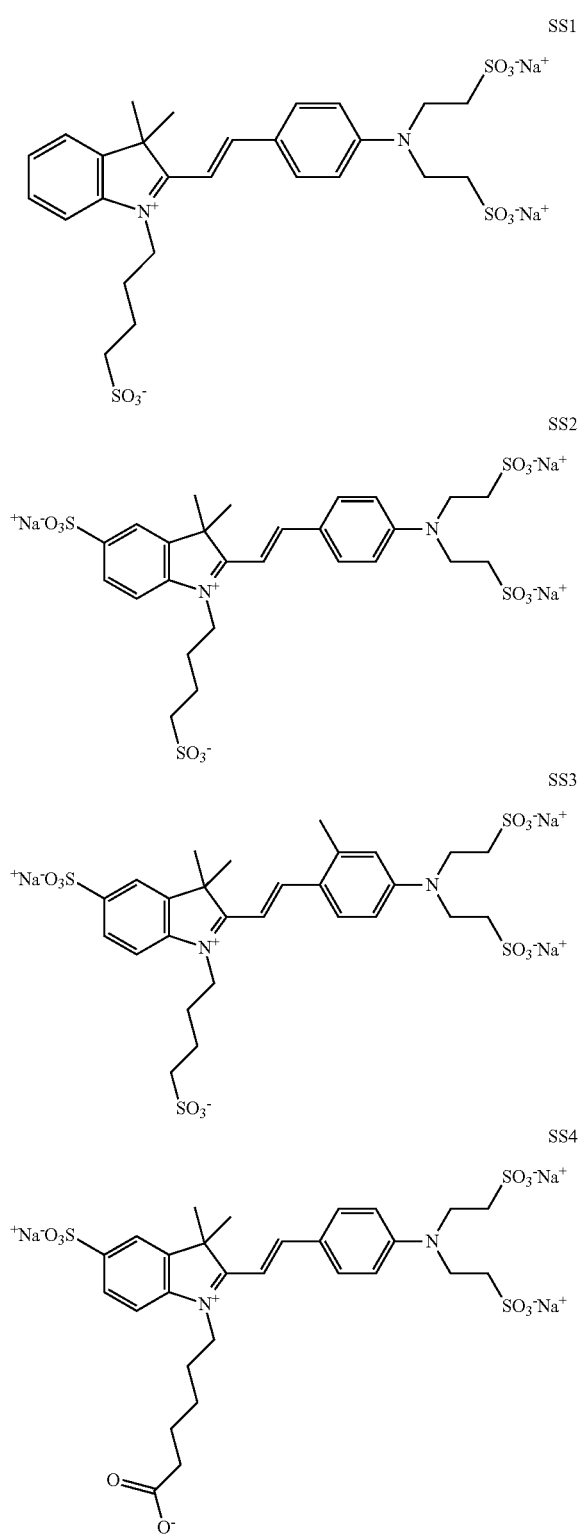

Example 3 illustrates characteristic absorbance spectra for compounds of the present disclosure.

Figure 1B:
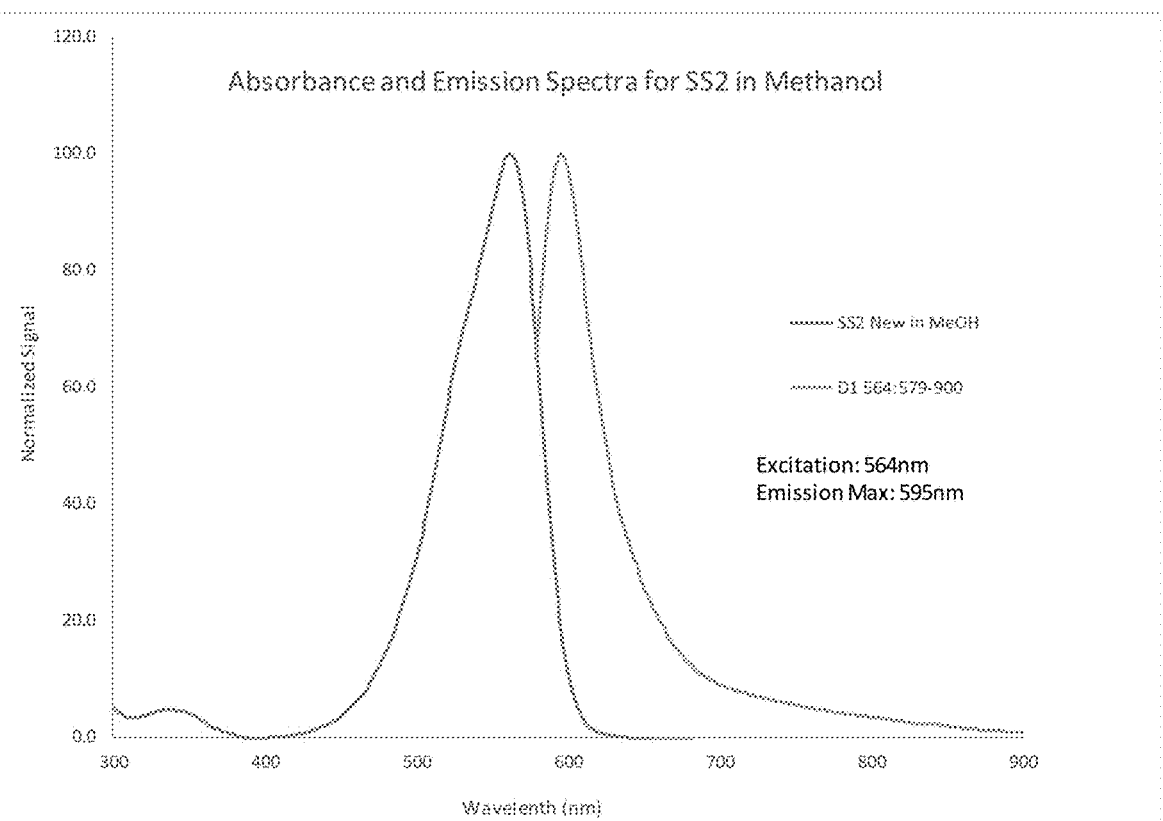

Concentrated stock solutions of compound SS2 and compound SS3 in methanol were prepared. Sub-stock solutions in methanol and acetic acid/methanol were prepared. Afterwards, the absorbance spectra of sub-stock solutions using a UV/Vis spectrophotometer were measured. The sub-stock solutions were diluted to approximately equal absorbance at 564 nm in methanol and acetic acid/methanol. FIGS. 1A and 1B are fluorescence spectra of SS2 in acetic acid/methanol and in methanol, respectively of diluted sub-stock solutions measured using a PTI fluorometer; set excitation at absorbance max (564 nm); scan emission to 579-900 nm.

Figure 2A:
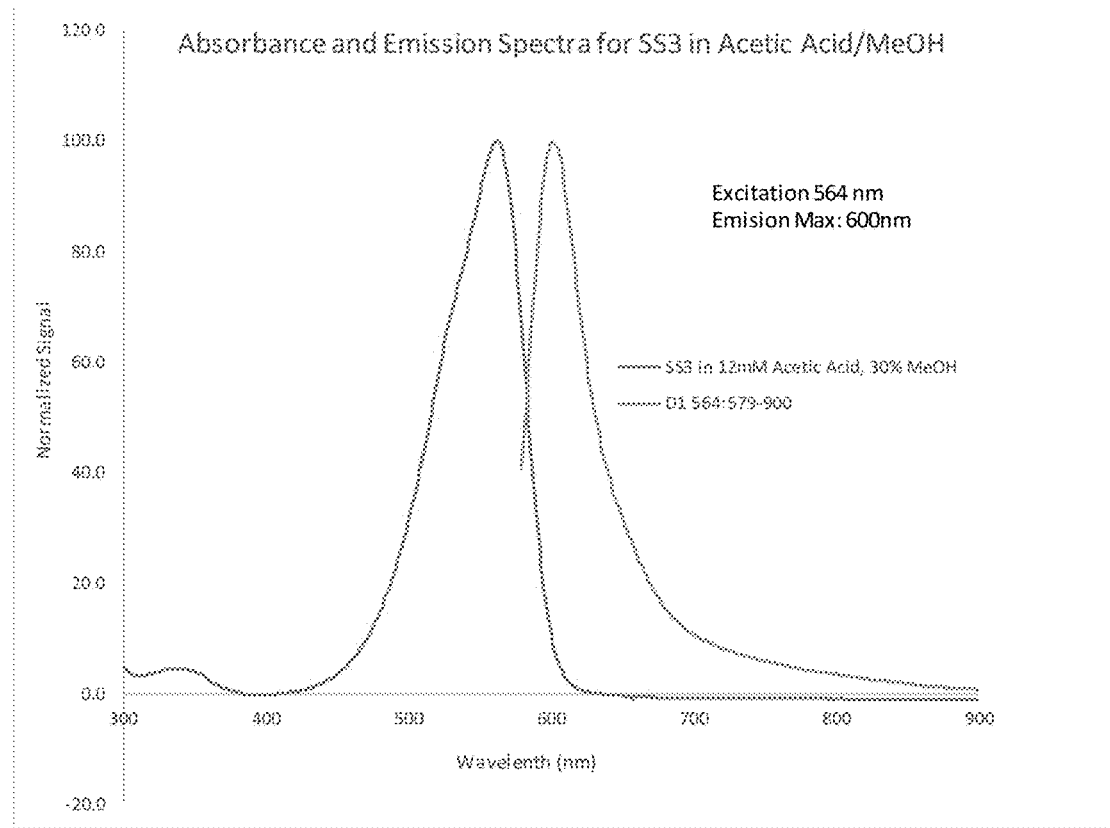
FIGS. 2A-2B show fluorescence spectra of a compound embodied in this disclosure.
Figure 2B:
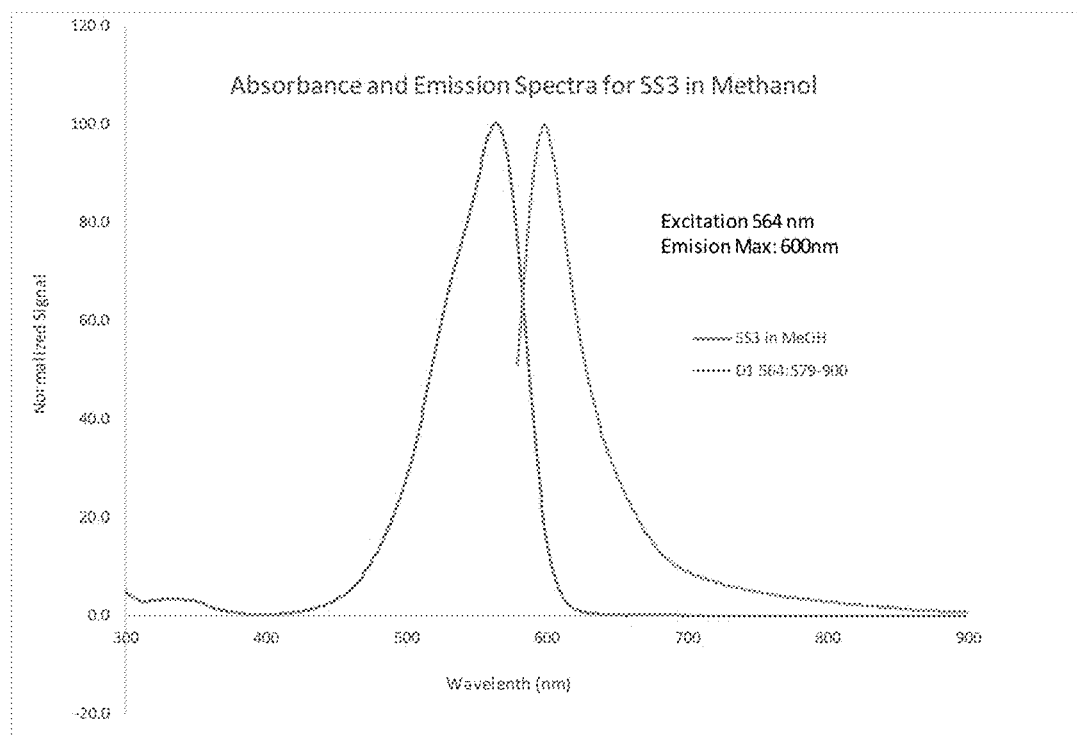

Similarly, FIGS. 2A and 2B are fluorescence spectra of SS3 in acetic acid/methanol and methanol, respectively of diluted sub-stock solutions measured using a PTI fluorometer; set excitation at absorbance max (564 nm); scan emission to 579-900 nm.

Example 4 illustrates concentrated dependent responses of a compound of the present disclosure on membranes.

Separate dilutions of C32 Cell Lysate (Santa Cruz Biotech) were made on 4-12% Novex BisTris Polyacrylamide Gels using a MES-SDS Running Buffer. After separation, the proteins were transferred to Nitrocellulose (NCM) or PVDF membranes using a BioRad TransBlot Turbo system.

A SS2 stain stock solution was prepared at approximately 120 μM concentration in methanol. From this stock solution, approximately 1.2 and 2.4 μM staining solutions were prepared in 6.67% acetic acid, and 30% methanol. The PVDF membrane was wetted briefly in methanol and transferred using ULTRApure water. Similarly, the NCM was wetted in ULTRApure water. The membranes were placed in stain solution for 5 to 10 minutes with gentle shaking. The stain was discarded and the membranes rinsed with wash buffer (6.67% acetic acid, 30% methanol) for 5-10 minutes. The membranes were rinsed with ULTRApure water and imaged on a LI-COR Odyssey Fc Imaging System using the 600 nm channel.

Figure 3A:
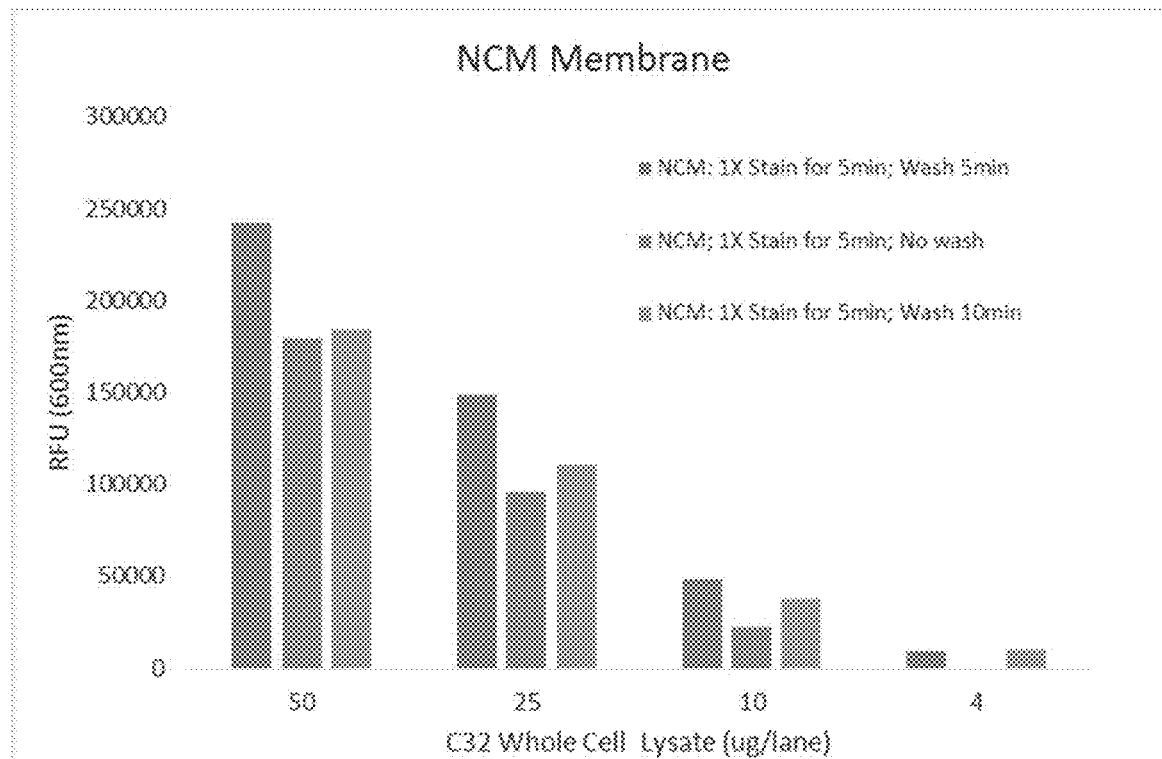
FIGS. 3A-3B show a signal from a compound embodied in this disclosure with 32 Cell lysate immobilized and stained on a NCM membrane with and without wash.
Figure 3B:
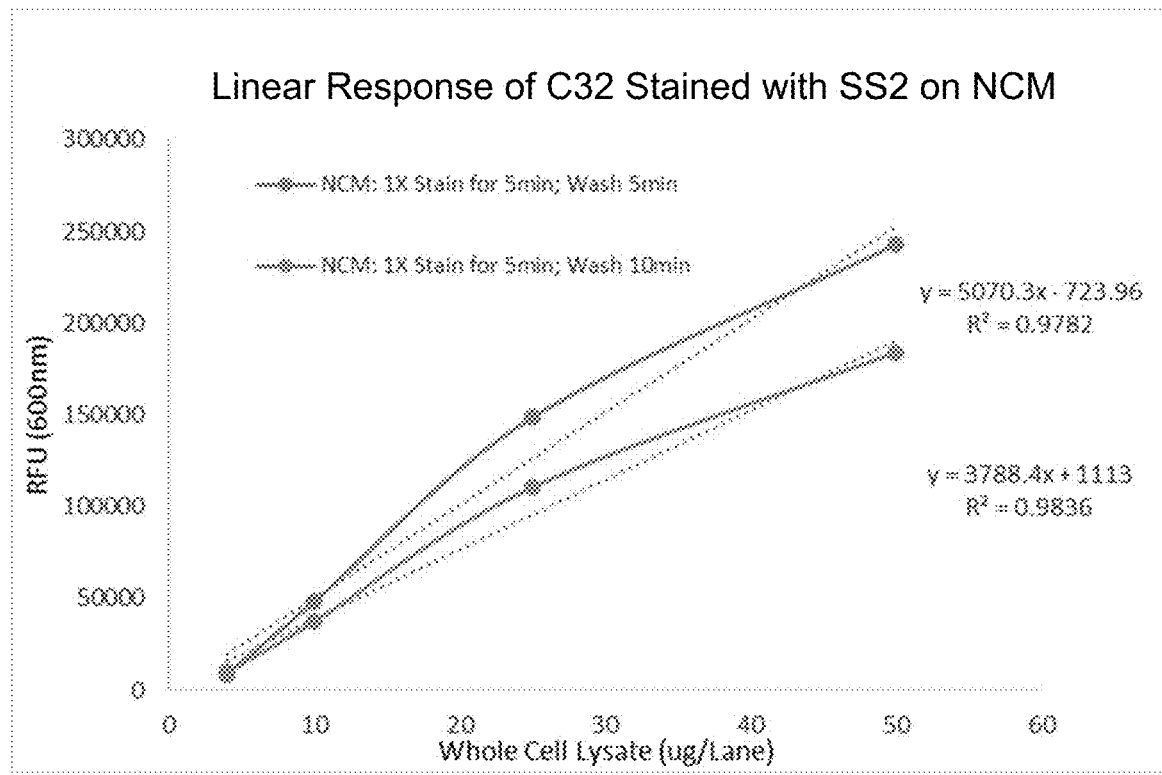

FIG. 3A shows a SS2 signal of 32 Cell lysate immobilized and stained on a NCM membrane with and without wash. As shown in FIG. 3B, the signal was linear from 4-50 μg, which provides a wide dynamic linear range.

Figure 3C:
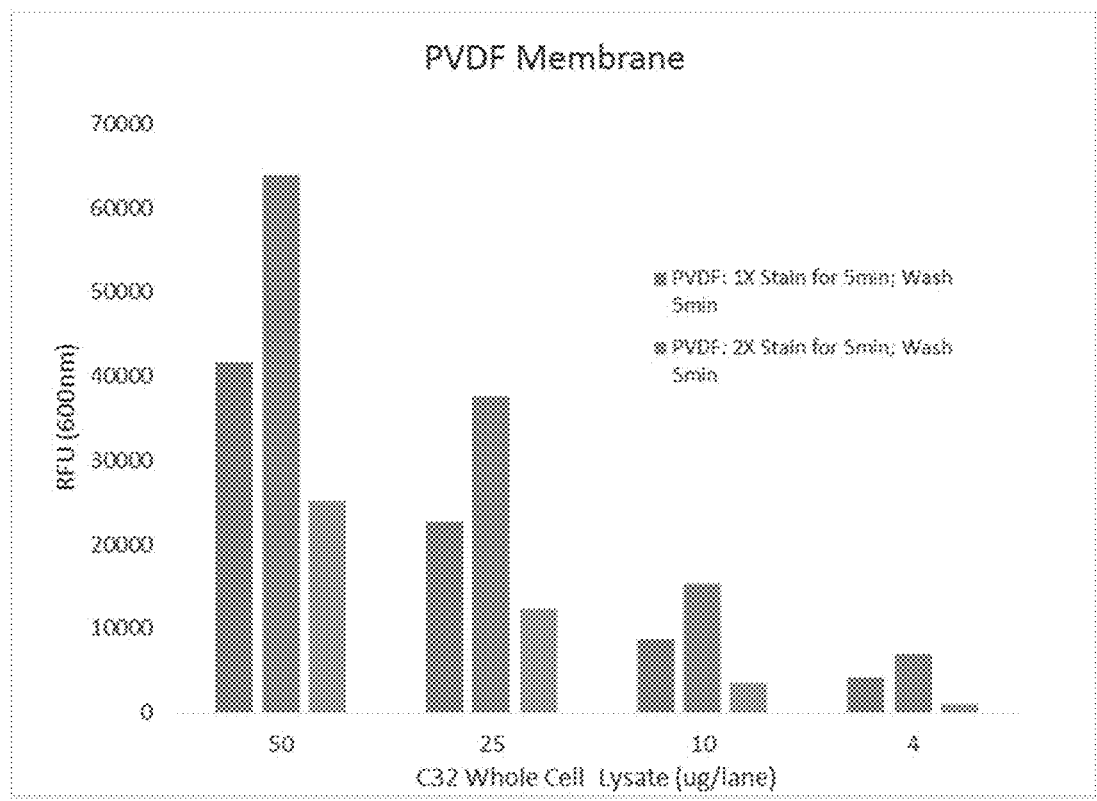
FIGS. 3C-3D show a signal from a compound embodied in this disclosure with 32 Cell lysate immobilized and stained on a PVDF membrane with and without wash.
Figure 3D:
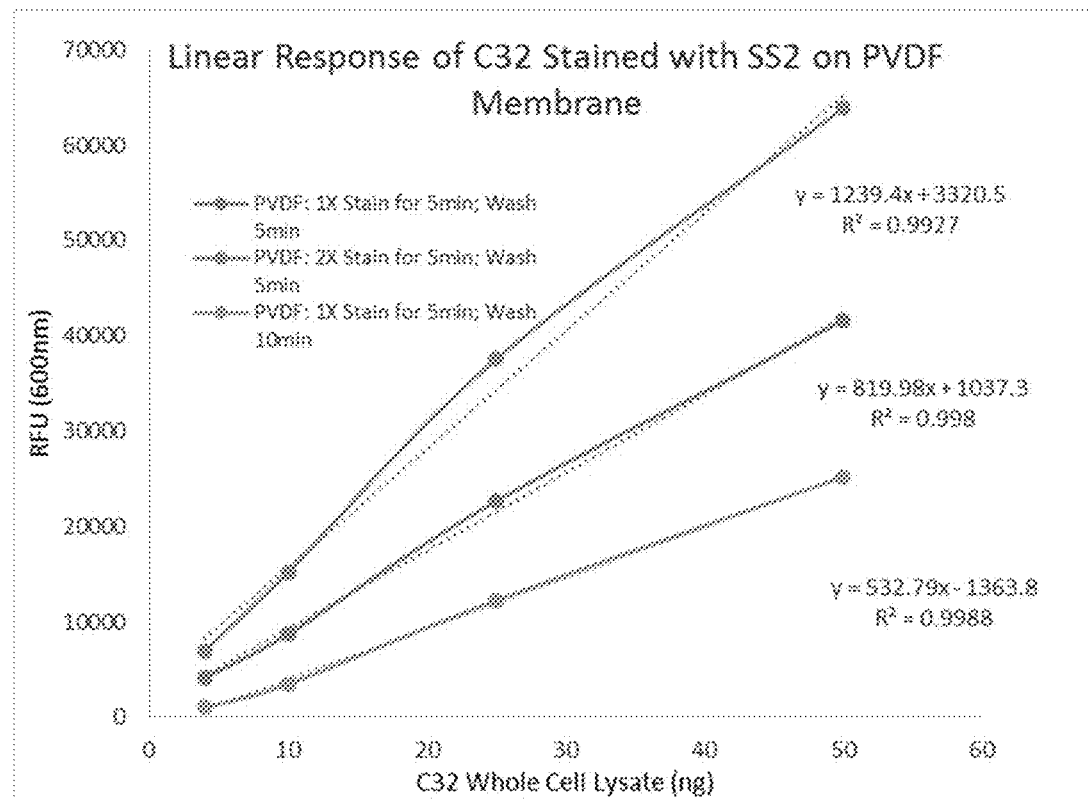

FIG. 3C shows a SS2 signal for 32 Cell lysate immobilized and stained on a PVDF membrane with and without wash. As shown in FIG. 3D, the signal was linear from 4-50 μg, which provides a wide dynamic linear range.

Example 5 illustrates that the stained protein signal is linear for at least 1 hour.

Figure 4:
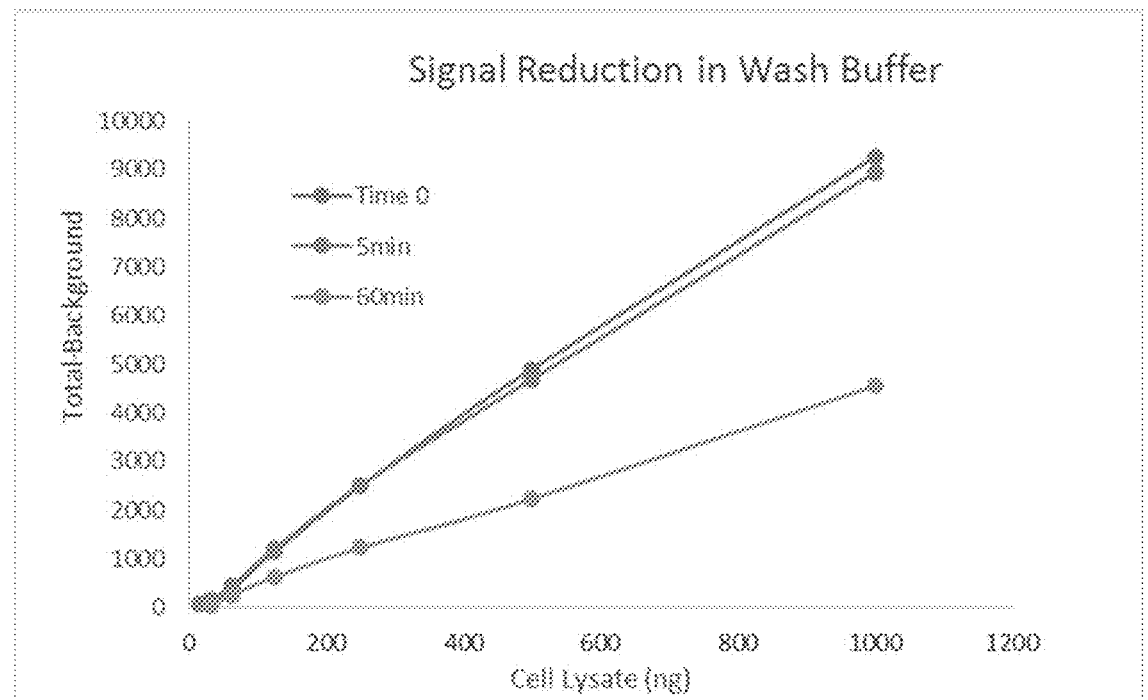
FIG. 4 shows the linearity of a protein signal stained with a compound embodied in this disclosure was maintained for at least 1 hour.

As shown in FIG. 4, the linearity of the SS2-Protein signal in acetic acid/methanol was maintained for at least 1 hour. A stock solution of BSA from GBiosciences (2000 ng/μL) was diluted to 500 ng/μL (1:4). Thereafter, twelve 2 fold serial dilutions from 500 ng/uL sub-stock were prepared. A 2 μL aliquot was spotted of each concentration on NCM strips and air dried. The membrane was wetted with ULTRApure Water. A SS2 stain stock solution was prepared at approximately 120 μM concentration in methanol. Prepare approximately 1.2 μM staining solutions in 6.67% acetic acid, and 30% methanol. The membranes were stained for 10 min with gentle mixing; the membranes were washed with acetic acid/methanol for 5 min and then imaged on Odyssey Fc. The membranes were stored in wash solution for up to 1 hour; image after 5 min and 60 min in wash solution. Advantageously, the SS2 signal linearity was maintained for 60 minutes.

Example 6 illustrates pH effects of protein staining.

A. Stain Binds at Low pH.

Figure 5:
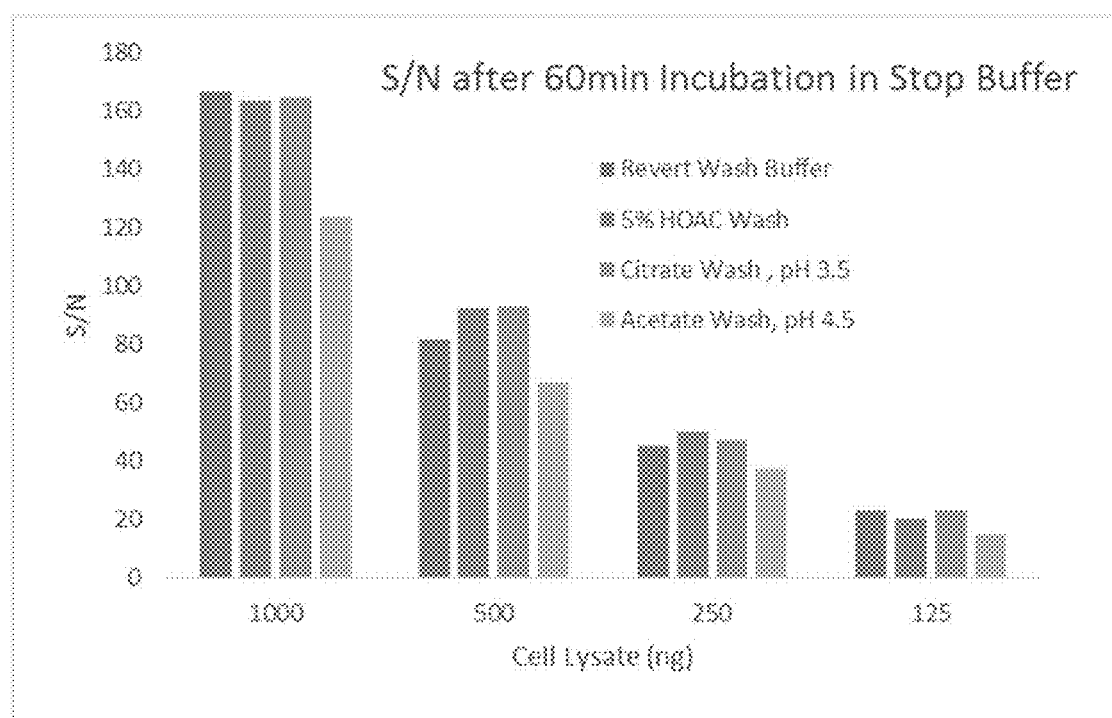
FIG. 5 shows the S/N of a protein signal stained with a compound embodied in this disclosure was maintained over the pH range 2-4.5.

The dyes (e.g., SS2) bind proteins at low pH. Any loss of signal when SS2 stained membranes are stored in ULTRApure water can be mitigated by storage in low pH buffers. Samples were spotted on NCM as noted above. Briefly, a stock solution of BSA from GBiosciences (2000 ng/μL) is diluted to 500 ng/μL (1:4) and twelve 2 fold serial dilutions from 500 ng/uL sub-stock are prepared. A 2 μL aliquot is spotted of each concentration on NCM strips and allowed to air dry. The membrane is wetted with ULTRApure Water. A SS2 stain stock solution is prepared at approximately 120 µM concentration in methanol and approximately 1.2 µM staining solutions is prepared in 6.67% acetic acid, and 30% methanol. The membranes are stained for 10 min with gentle mixing. The membranes are stored in wash solution (6.67% acetic acid, 30% methanol), 5% Acetic Acid, 50 mM Sodium Citrate pH 3.5 and 50 mM Sodium Acetate pH 4.5. Thereafter, the membranes are imaged on an Odyssey Fc immediately and for up to 60 minutes storage. The Signal/Noise ratio as [Total Signal-Total Background]/[StandDeviation Background] is then calculated. As shown in FIG. 5, the S/N was maintained over the pH range 2-4.5.

B. Stain Reverses at High pH

The SS2 stain can be removed from proteins at high pH. The most efficient removal is achieved by addition of methanol to the basic buffer. Briefly, dilute a stock solution of BSA from GBiosciences (2000 ng/µL) to 500 ng/µL (1:4); prepare seven 2 fold serial dilutions from 500 ng/µL sub-stock. Spot 2 µL of each concentration on NCM strips; air dry. Wet membrane with ULTRApure Water. Prepare SS2 stain stock solution at approximately 120 µM concentration in methanol; prepare approximately 4 µM staining solution in 6.67% acetic acid, 30% methanol. Stain membranes for 5 min with gentle mixing; wash membranes for 5 minutes with 6.67% acetic acid, 30% methanol; and rinse membranes in ULTRApure water (Control). Store membranes in Reversal Solutions* for up to 1 hour. Image on Odyssey Fc immediately and for up to 60 minutes storage. Calculate [Signal-Mean Background] at 1000 ng. The best stain removal is achieved in sodium hydroxide with methanol (pH>10).

C. Reversal Solutions

Figure 6:
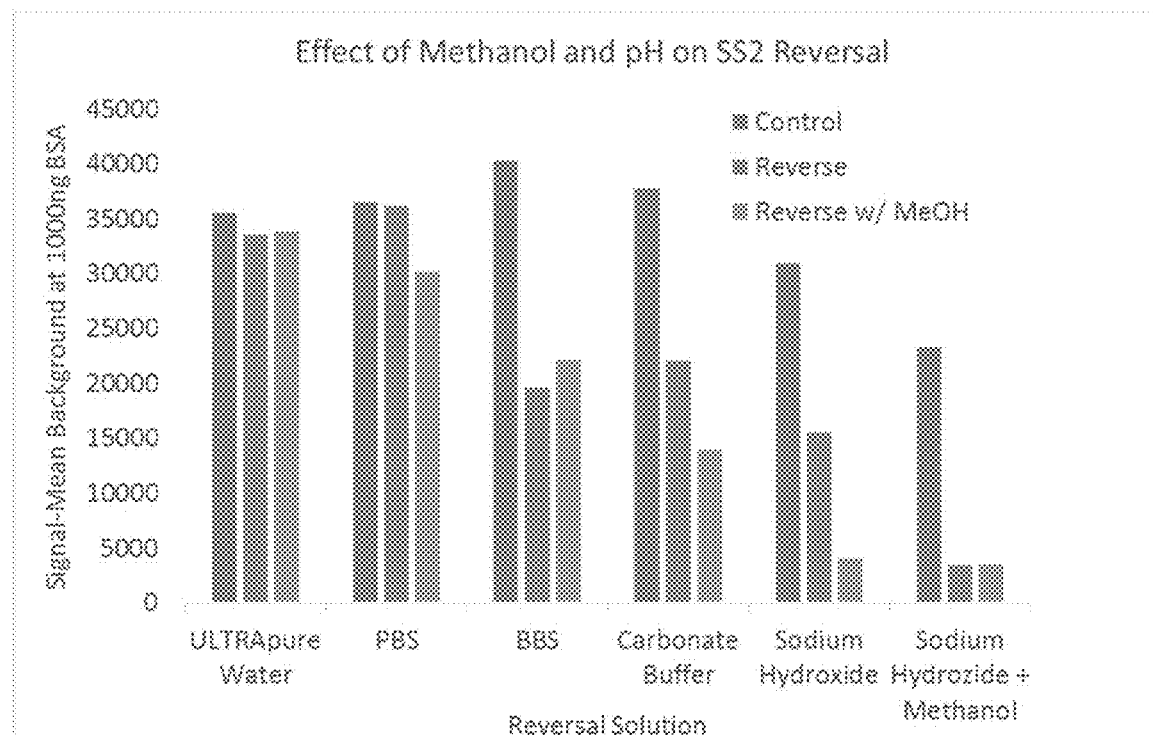
FIG. 6 shows a protein signal stained with a compound embodied in this disclosure is reversible.

Various reversal solutions are shown in FIG. 6:
i. ULTRApure Water
ii. PBS, pH 7.4: Phosphate Buffered Saline, 10 mM $PO_4^{3-}$, 137 mM NaCl, and 2.7 mM KCl, pH 7.4
iii. BBS pH 8.5: Borate Buffered Saline, 0.010 M borate buffer, 0.15 M NaCl, pH 8.2
iv. Carbonate Buffer: 0.1M $NaHCO_3$ pH 9.5
v. Sodium Hydroxide: 0.1M NaOH, 0.1M, pH >10
vi. Sodium Hydroxide+Methanol: 0.1M NaOH, 30% (v/v) Methanol, pH >10.

Example 7 illustrates that the stain does not affect immunodetection.

The stain does not affect downstream processing and immunodetection. In this example, Western blots were performed after total protein staining using SS2. Briefly, separate dilutions of C32 Cell Lysate (Santa Cruz Biotech) on 4-12% Novex BisTris Polyacrylamide Gels using MES-SDS Running Buffer were prepared. After separation, the proteins were transferred to nitrocellulose (NCM) or PVDF membranes using a BioRad TransBlot Turbo system. SS2 stain stock solution at approximately 120 µM concentration in methanol was prepared and approximately 5, 10 and 15 µM staining solutions were prepared in 6.67% acetic acid, 30% methanol.

The PVDF membranes were briefly wetted in methanol and transferred to ULTRApure water for 5 minutes. The NCM membrane was wetted in ULTRApure water for 5 minutes. The water was discarded from the membranes and 5 mL of stain solution was added. Incubate for 5 minutes with gentle shaking. Discard the stain solution. Wash membranes with 6.67% acetic acid, 30% methanol for 5 min with gentle agitation. Rinse membrane with ULTRApure water and image on a LI-COR Odyssey Fc Imaging System using the 600 nm channel.

Membranes were wetted in PBS for 5 minutes with gentle shaking. A fresh set of unstained NCM and PVDF membranes were wetted as outlined above for use as Controls. Membranes were transferred to Odyssey Blocking Buffer (OBB) and block overnight at 4° C. The blocking buffer was discarded and processed using a typical Western Blot protocol with 1 hour primary antibody incubation (β-Actin Rabbit mAb, LI-COR P/N 926-42210, 1:1000 in OBB) and 1 hour secondary antibody incubation (Goat anti-Rabbit-IRDye 800CW, LI-COR P/N 926-32111) diluted 1:10,000 in OBB+0.1% Tween 20. Image blots of Odyssey Fc using 800 Channel.

Figure 7A:
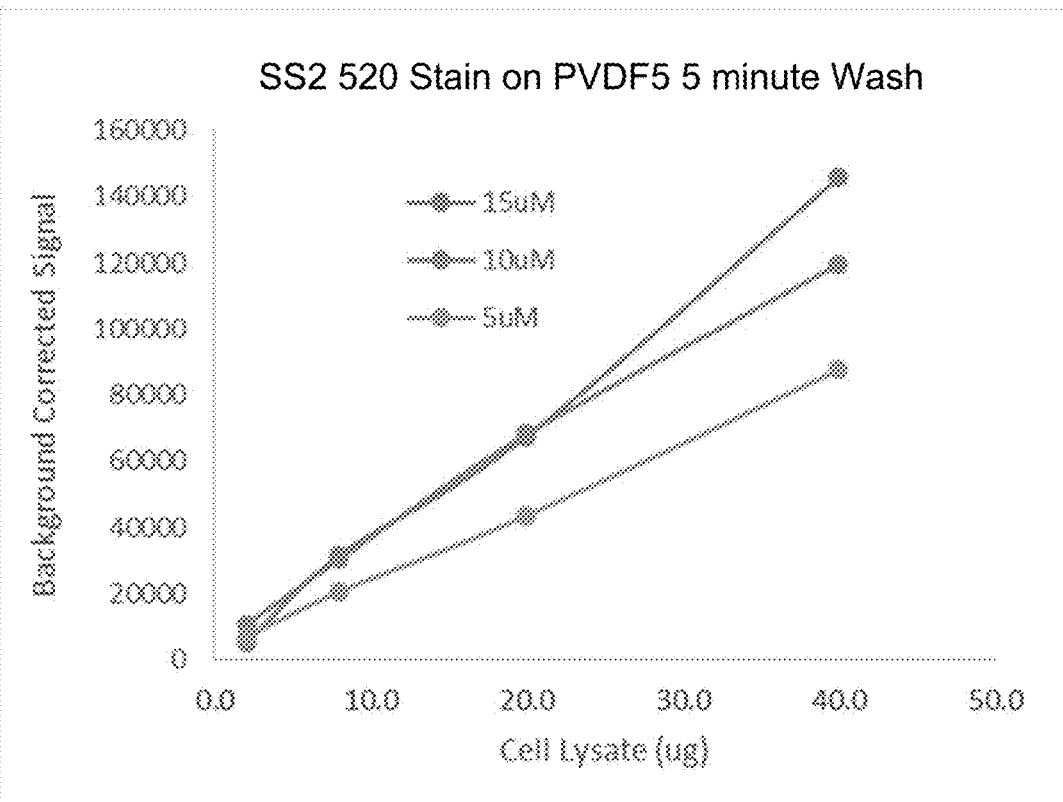
FIGS. 7A-7B show signals for 32 Cell lysate immobilized and stained on both NCM and PVDF membranes respectively, were linear.
Figure 7B:
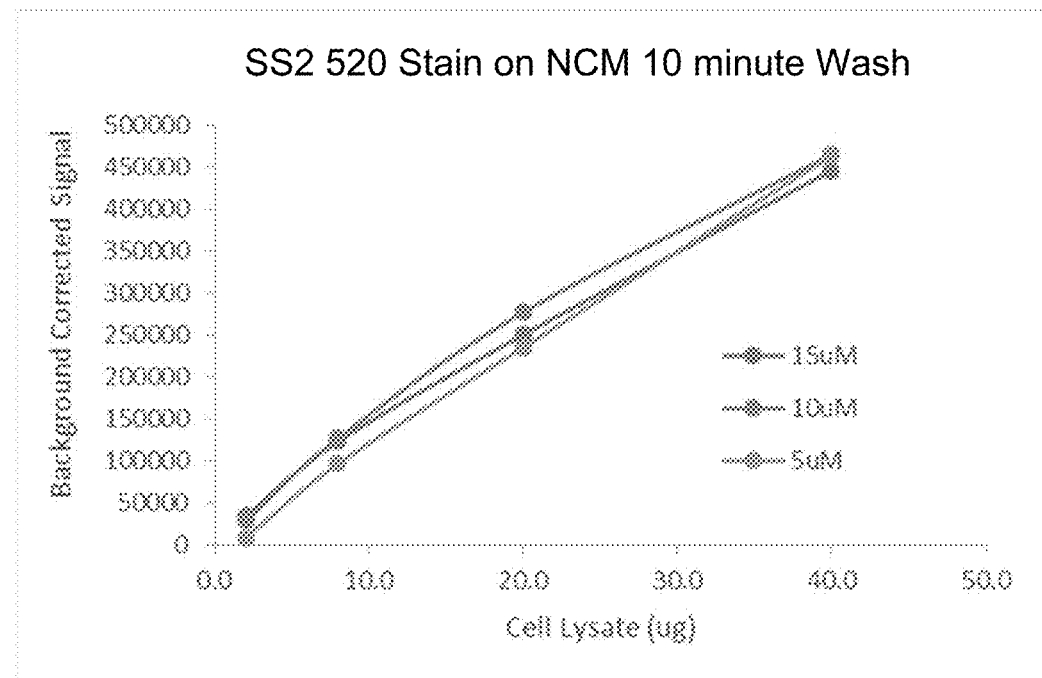
Figure 8A:
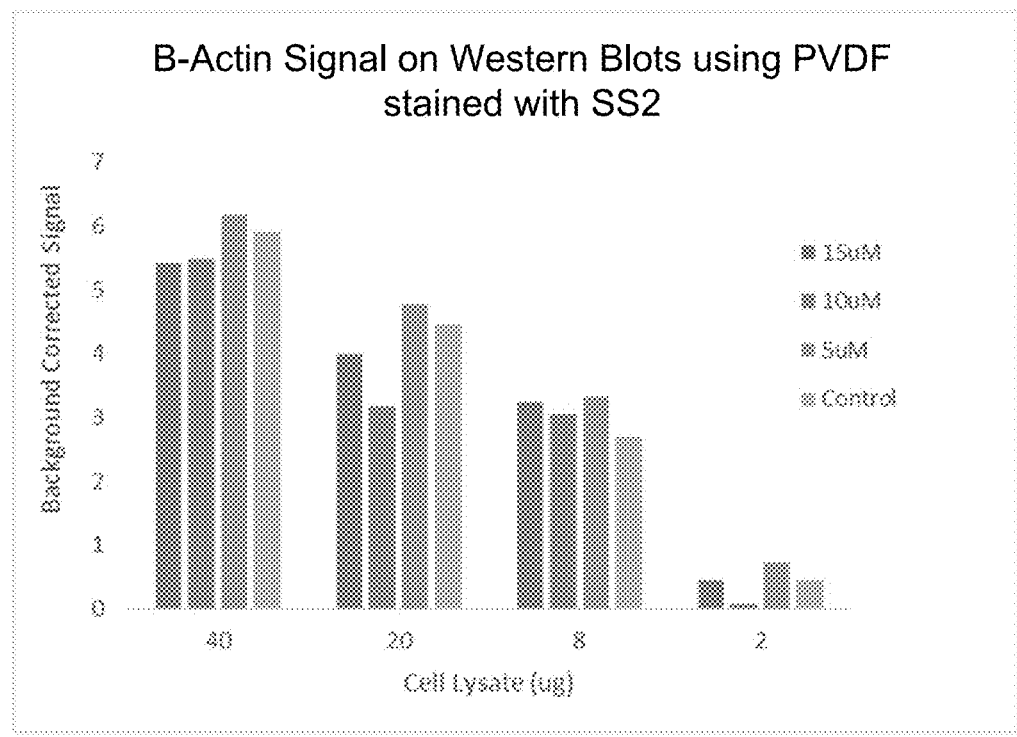
FIGS. 8A-8B show a β-actin signal was unaffected by staining with SS2 as control (unstained) and FIG. 8B, test (stained) membranes.
Figure 8B:
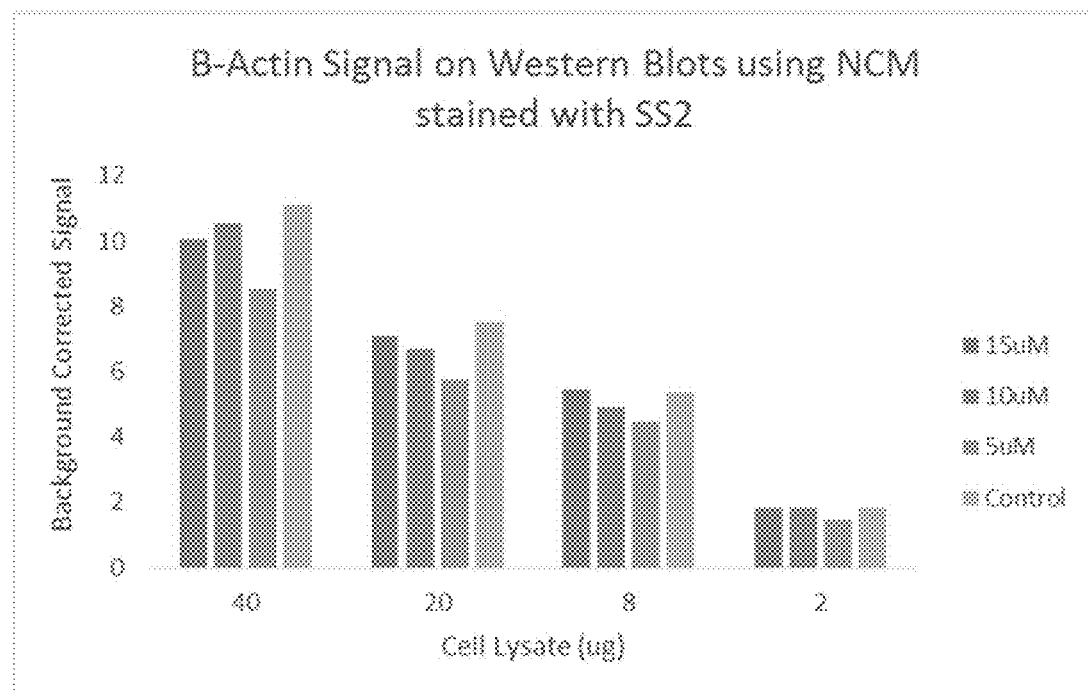

As shown in FIGS. 7A-7B, the signals for 32 Cell lysate immobilized and stained on both NCM and PVDF membranes were linear from 4-50 µg cell lysate amounts using 5-15 µM SS2, although different wash times were used to produce a linear response at the same SS2 concentrations. As shown in FIG. 8A, the β-actin signal was unaffected by staining with SS2 as control (unstained) and FIG. 8B, test (stained) membranes displayed essentially the same signal intensity in the 800 channel on Fc.

Example 8 illustrates that the inventive stains are useful for multiplexing.

Figure 9A:
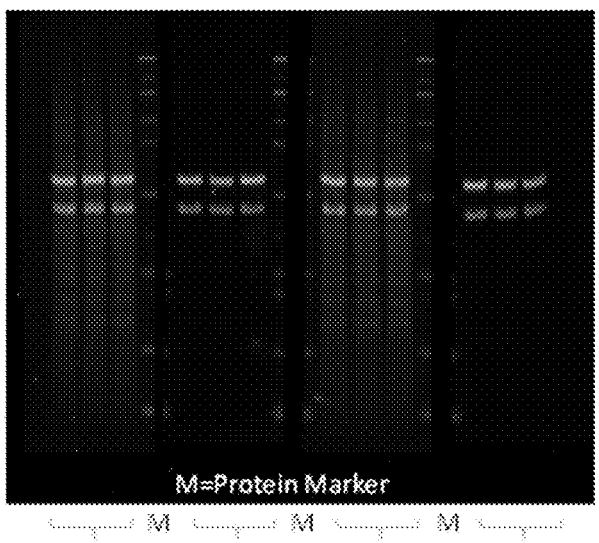

In multiplexing experiments where two targets are visualized in the near IR (NIR) using appropriate fluorophores, the SS2 total protein stain can be used in a third channel with visible signal at 554 nm. Briefly, C32 cell lysate (10 µg/lane) was separated on multiple SDS-PAGE gels and transferred to NCM and PVDF membranes. The membranes were stained with approximately 12 µM SS2 in 6.67% acetic acid, 30% methanol for 5 min. Excess stain was removed by washing the membranes in acetic acid/methanol and the membranes were images on a LI-COR Odyssey Fc in the 600 nm channel. Membranes were subsequently processed through a Western Blot procedure using α-Tubulin and 13-Actin primary antibodies (1:1000 in LI-COR Odyssey Blocking Buffer) and IRDye 800CW Goat anti-Rabbit and IRDye 680RD Goat anti-Mouse secondary antibodies (1:10, 000 in Odyssey Blocking Buffer with 0.1% Tween 20). Blots were washed in PBST and imaged on an Odyssey Fc in the 700 and 800 nm channels (see FIG. 9). Control membranes, not stained with SS2 were included. The β-Actin and α-Tubulin signals were unaffected by staining with SS2 as control (unstained) and test (stained) membranes displayed essentially the same signal intensity in the 700 and 800 channel on Fc. (see, FIG. 9B)

Example 9 illustrates that proteins can be stained in a SDS-PAGE matrix.

As shown in FIGS. 10A-D, proteins can be stained in a SDS-PAGE matrix. Briefly, load 10 µg of denatured C32 Cell lysate in 4 lanes of a 4-12% BisTris Gel, place a molecular weight marker in alternate lanes (LI-COR P/N 928-60000) and electrophorese proteins using standard conditions. Fix proteins in the gel matrix for 1 hour by incubating the gel in a solution of 10% acetic acid and 30% methanol with gentle agitation. Discard the fix solution. Prepare approximately 12 µM staining solution in 6.67% acetic acid, 30% methanol; add stain to the gel and incubate for 1 hour with gentle agitation. Discard the stain solution. Rinse the gel briefly several times with 6.67% acetic acid, 30% methanol; wash the gel for 1 hour in 6.67% acetic acid, 30% methanol; wash overnight in 6.67% acetic acid, 30% methanol. The protein bands from the C32 lysate are readily visible in the gel matrix. When imaged on an Odyssey Fc in 600 channel, the signal intensity is robust.

Example 10 shows staining data using two compounds of the disclosure.

In this example, compound SS1 and SS2 were tested for their staining characteristics. Their structures are set forth below.

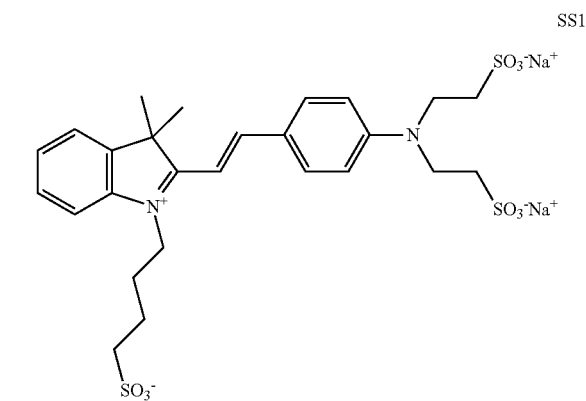

SS1

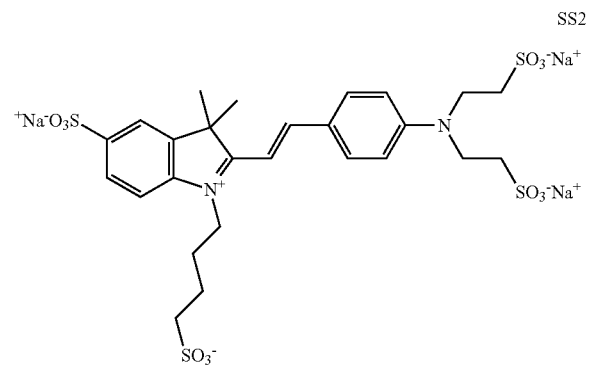

SS2

FIG. 11A and FIG. 11C shows the staining functionality of SS1 and its staining ability of BSA under the conditions tested. The characteristics of SS2 staining is shown in FIG. 11B and FIG. 11D. As shown, the staining is observable by fluorescence and visible light as indicated in FIG. 11B and FIG. 11D. The results from Odyssey Fc are a good indicator of the stain's utility having an excitation at 530 nm and emission wavelength at 580 nm.

Example 11 is a conjugation-reaction example.

In this example, compound SS4 is conjugated to an antibody.

Proteins can be conjugated to the NHS ester form of the 520 dye (SS4). Briefly, the SS4 520 NHS ester was synthesized per protocols described herein. For the conjugation, goat anti-mouse (GAM) IgG (0.8 and 8 mg/mL) was prepared in borate buffered saline at pH 8.5. To the IgG, 6 molar equivalents of SS4 NHS ester (MW 813.82, structure below) were added and the reaction, incubated at ambient temperature and protected from light for 2 hours. Unreacted dye was removed using Zeba desalt spin columns. The dye to protein ratio and the protein concentration of the purified product were determined spectrophoto-metrically. The amount of free dye in the purified product was determine by size exclusion chromatography. The results are shown in the table below. As expected, the labeling reaction was concentration dependent; a tenfold increase in GAM concentration resulted in a higher degree of labeling i.e. D/P 1.3 versus 1.9, respectively.

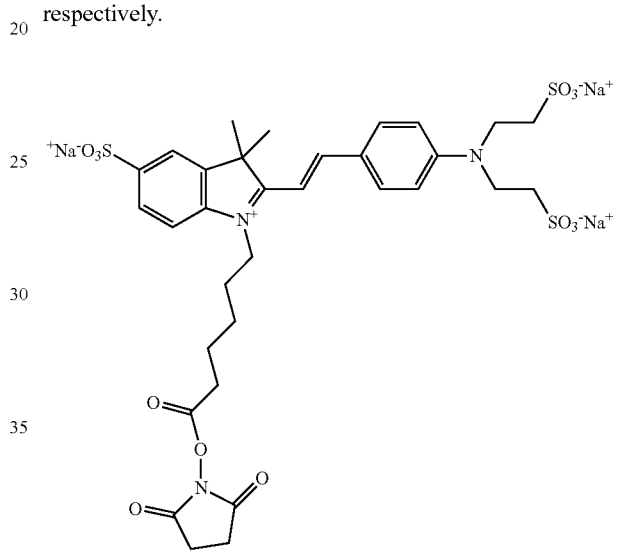

The SS4 NHS ester above reacts with a primary amine on the GAM IgG to yield an amide bond linking the SS4 dye.

| Exp 18: Test Conjugation Conditions for GAM and SS4 520 nm NHS ester | | | | | | | | | | | | | | |
|---|---|---|---|---|---|---|---|---|---|---|---|---|---|---|
| GAM in Labeling Rx. (mg/mL) | Dye Solvent | Results | Rep | A552 | A280 | DF | D/P | Mean D/P | Std Dev | Protein conc mg/mL | Mean Protein Conc (mg/mL) | Volume (mL) | Mass (mg) | % Free Dye |
| 1 mg/mL | DW | GAM1 | 1-1 | 0.22483 | 0.46611 | 2.0 | 1.3 | | | 0.63 | | | | |
| | | | 1-2 | 0.21909 | 0.45526 | 2.0 | 1.3 | 1.3 | 0.0 | 0.62 | 0.62 | 1.20 | 0.75 | 2.9 |
| | | | 1-3 | 0.22148 | 0.46034 | 2.0 | 1.3 | | | 0.62 | | | | |
| | BBS' | GAM2 | 2-1 | 0.20848 | 0.44774 | 2.0 | 1.3 | | | 0.61 | | | | |
| | | | 2-2 | 0.20862 | 0.44875 | 2.0 | 1.3 | 1.3 | 0.0 | 0.61 | 0.60 | 1.20 | 0.73 | 3.5 |
| | | | 2-3 | 0.2073 | 0.44481 | 2.0 | 1.3 | | | 0.60 | | | | |
| | DMSO | GAM3 | 3-1 | 0.18368 | 0.41429 | 2.0 | 1.2 | | | 0.56 | | | | |
| | | | 3-2 | 0.18627 | 0.42377 | 2.0 | 1.2 | 1.2 | 0.0 | 0.57 | 0.57 | 1.20 | 0.69 | 3.6 |
| | | | 3-3 | 0.18788 | 0.42686 | 2.0 | 1.2 | | | 0.58 | | | | |
| 10 mg/mL | DW | GAM4 | 1-1 | 0.33903 | 0.50393 | 2.0 | 1.9 | | | 0.67 | | | | |
| | | | 1-2 | 0.34209 | 0.51142 | 2.0 | 1.9 | 1.9 | 0.0 | 0.68 | 0.68 | 1.20 | 0.81 | 2.0 |
| | | | 1-3 | 0.34213 | 0.51147 | 2.0 | 1.9 | | | 0.68 | | | | |
| | BBS* | GAM5 | 1-1 | 0.32894 | 0.50281 | 2.0 | 1.8 | | | 0.67 | | | | |
| | | | 1-2 | 0.32962 | 0.50443 | 2.0 | 1.8 | 1.8 | 0.0 | 0.67 | 0.68 | 1.20 | 0.81 | 2.0 |
| | | | 1-3 | 0.33267 | 0.51049 | 2.0 | 1.8 | | | 0.68 | | | | |
| | DMSO | GAM6 | 1-1 | 0.30586 | 0.47872 | 2.0 | 1.8 | | | 0.64 | | | | |
| | | | 1-2 | 0.30739 | 0.48152 | 2.0 | 1.8 | 1.8 | 0.0 | 0.64 | 0.64 | 1.20 | 0.77 | 2.1 |
| | | | 1-3 | 0.30885 | 0.48617 | 2.0 | 1.8 | | | 0.65 | | | | |

Although the foregoing disclosure has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A compound having Formula I:

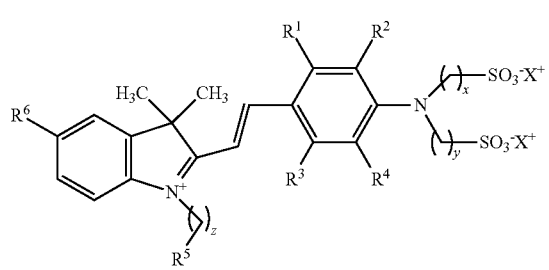

wherein $R^1$, $R^2$, $R^3$, $R^4$, $R^5$ and $R^6$ are each a member independently selected from the group consisting of hydrogen, alkyl, alkenyl, halo, hydroxyl, alkoxy, amino, cyano, carboxyl, carboxylate, alkoxycarbonyl, amido, sulfonato, alkoxyalkyl, carboxyalkyl, alkoxycarbonylalkyl, sulfonatoalkyl, a functional group for conjugation to a biomolecule, and $R^7B$, wherein $R^7$ is the resultant attachment between the compound and a biomolecule;

B is a biomolecule selected from the group consisting of a protein, a peptide, a hormone, an antibody or a fragment thereof, an antigen, a hapten, an avidin, a streptavidin, a carbohydrate, a carbohydrate derivative, an oligosaccharide, a polysaccharide, a nucleic acid, a deoxynucleic acid, a fragment of DNA, a fragement of RNA, a nucleotide triposphatase, an acyclo terminator triphosphatase, and a peptide nucleic acid (PNA);

x, y and z are each an integer independently selected from 1-10; and

X is hydrogen or a metal cation, wherein said compound has a balanced charge, wherein in Formula I, at least one of $R^1$, $R^2$, $R^3$, $R^4$, $R^5$ and $R^6$ is a functional group for conjugation, which is a member selected from the group consisting of a maleimide, an activated acyl, an activated ester, N-hydroxysuccinimidyl, a hydrazine, a hydrazide, a hydrazone, an azide, an alkyne, an aldehyde, a thiol, and protected groups thereof for conjugation or is $R^7B$.

2. The compound of claim 1, wherein $R^1$, $R^2$, $R^3$, $R^4$ and $R^5$ are each a member independently selected from the group consisting of hydrogen, alkyl, halo, hydroxyl, alkoxy, carboxyl, alkoxycarbonyl, amido, and sulfonato.

3. The compound of claim 1, wherein $R^1$, $R^2$, $R^3$, $R^4$ and $R^5$ are each a member independently selected from the group consisting of hydrogen and alkyl.

4. The compound of claim 1, wherein $R^6$ is a member selected from the group consisting of hydrogen, alkyl and sulfonato.

5. The compound of claim 1, wherein the functional group for conjugation to a biomolecule is a member selected from the group consisting of a maleimide, an activated acyl, an activated ester, N-hydroxysuccinimidyl, an azide, an alkyne, an aldehyde, a thiol, and protected groups thereof for conjugation to a biomolecule.

6. The compound of claim 5, wherein $R^5$ is the functional group for conjugation to a biomolecule or is $R^7B$.

7. The compound of claim 1, wherein the compound has the formula selected from the group consisting of:

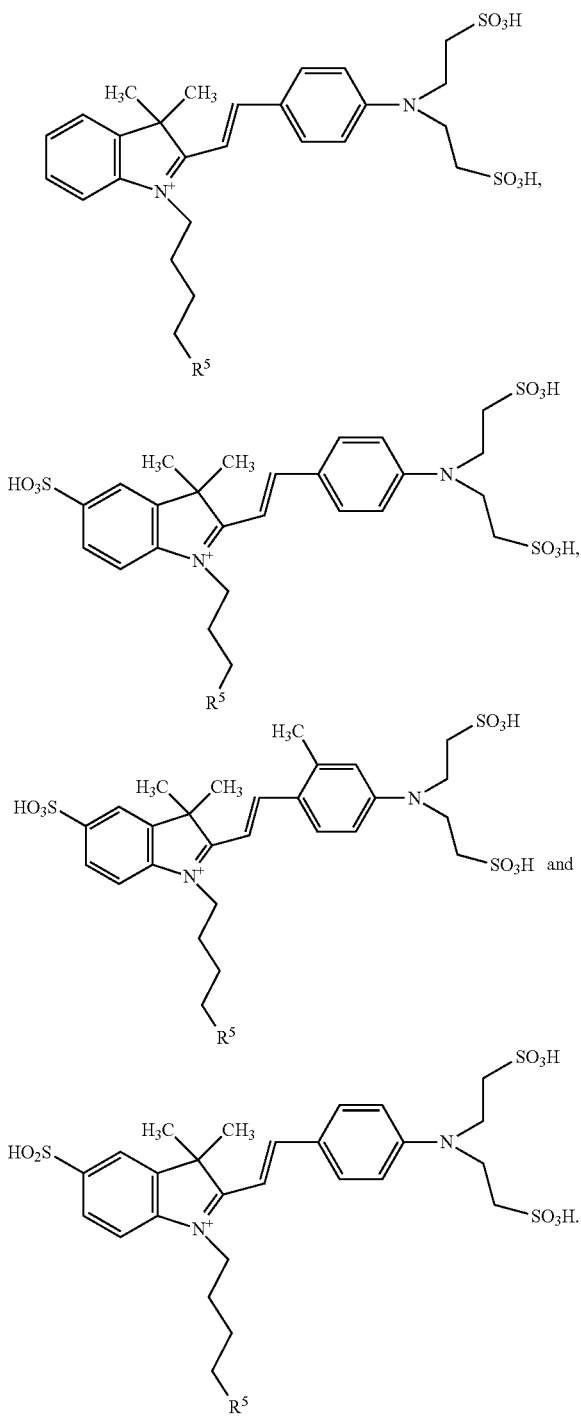

8. A method for detecting and/or staining a protein, the method comprising:

contacting a staining mixture that contains a compound or dye of

Formula I according to claim 1;

with a protein to form a combined mixture;

incubating the combined mixture for a time sufficient for the compound or dye of Formula I to associate with the protein to form a dye complex that gives an optical response upon illumination;

illuminating the dye-protein complex; and detecting the optical response.

9. The method of claim 8, wherein the dye complex association is reversible.

10. The method of claim 8, wherein the dye complex association is performed at an acidic pH.

11. The method of claim 10, wherein the acidic pH is in a range of 1 to 6.

12. A kit for staining a protein in a sample, the kit comprising:

a) a compound or dye:

of Formula I(a) :

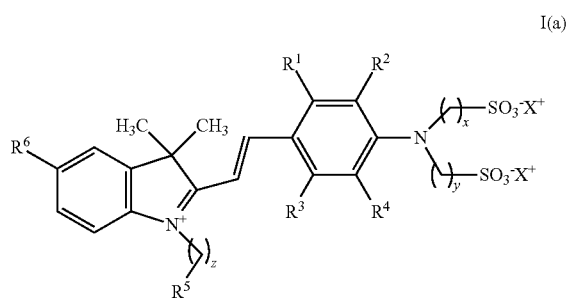

wherein $R^1$, $R^2$, $R^3$, and $R^4$ are each hydrogen;

$R^5$ is a member selected from the group consisting of hydrogen, alkyl, alkenyl, halo, hydroxyl, alkoxy, amino, cyano, carboxyl, carboxylate, alkoxycarbonyl, amido, sulfonato, alkoxyalkyl, carboxyalkyl, alkoxycarbonylalkyl, and sulfonatoalkyl carboxylate and sulfonato;

$R^6$ is sulfonato;

x and y are each 2;

z is an integer selected from 3 or 4; and

X is hydrogen or a metal cation, wherein said compound or dye has a balanced charge; and b) instructions for combining said compound or dye of Formula I(a) with a sample containing a protein; said instructions comprising:

i) combining the sample with a staining mixture that contains said compound or dye of Formula I(a) to form a combined mixture; and ii) incubating the combined mixture for a time sufficient for the dye or compound in the staining mixture to associate with the protein in the sample mixture to form a dye-protein complex that gives a detectable optical response upon illumination.

13. A compound having Formula I(a):

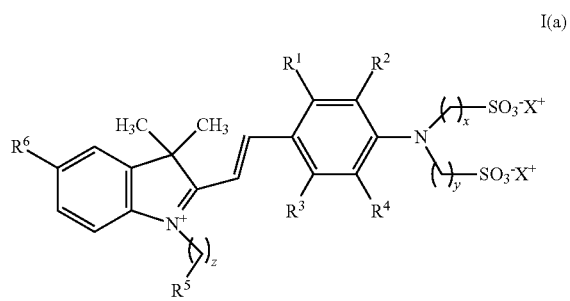

wherein $R^1$, $R^2$, $R^3$, and $R^4$ are each hydrogen or alkyl;

$R^5$ is a member selected from the group consisting of hydrogen, alkyl, alkenyl, halo, hydroxyl, alkoxy, amino, cyano, carboxyl, carboxylate, alkoxycarbonyl, amido, sulfonato, alkoxyalkyl, carboxyalkyl, alkoxycarbonylalkyl, and sulfonatoalkyl carboxylate and sulfonato;

$R^6$ is sulfonato;

x and y are each 2;

z is an integer selected from 3 or 4; and

X is hydrogen or a metal cation, wherein said compound has a balanced charge.

14. The compound of claim 13, wherein z is 3.

15. The compound of claim 13, wherein the compound has the formula selected from the group consisting of:

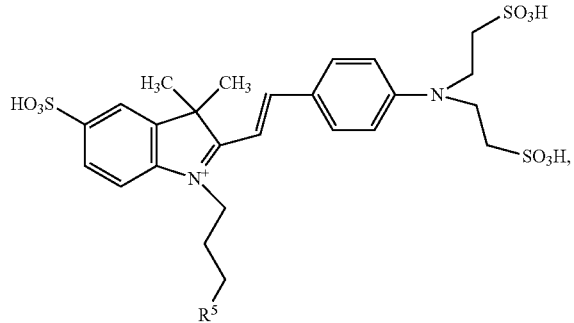

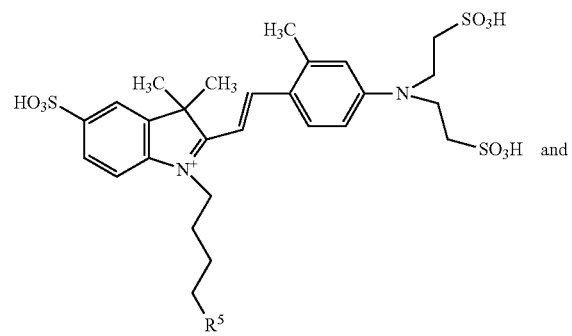

and

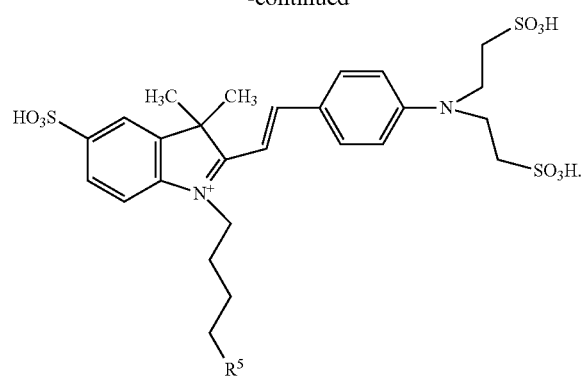

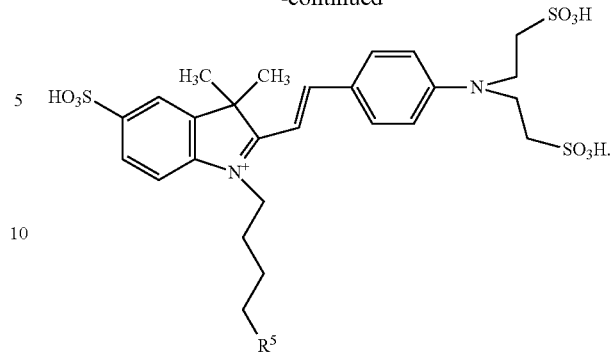

18. A compound having the formula:

16. A method for detecting and/or straining a protein, the method comprising:

contacting a staining mimxture that contains a compound or dye of Formula I(a) according to claim 13 with a protein to form a combined mixture;

incubatinig the combined mixture for a time sufficient for the compund or dye of Formula (Ia) to associate with the protein to form a dye complex that gives an optical response upon illumination;

illuminating the dye-protein complex; and detecting the optical response.

17. The method of claim 8, wherein the compound has the formula selected from the group consisting of:

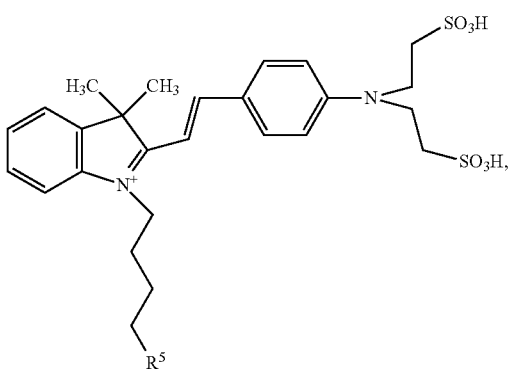

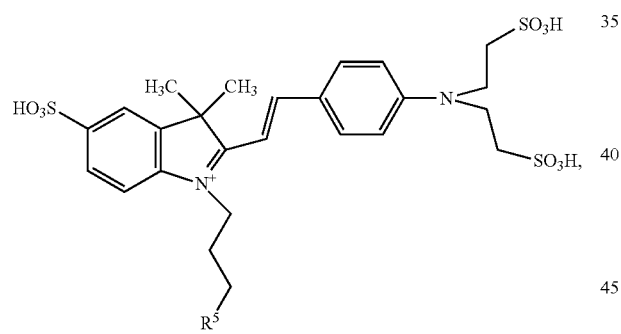

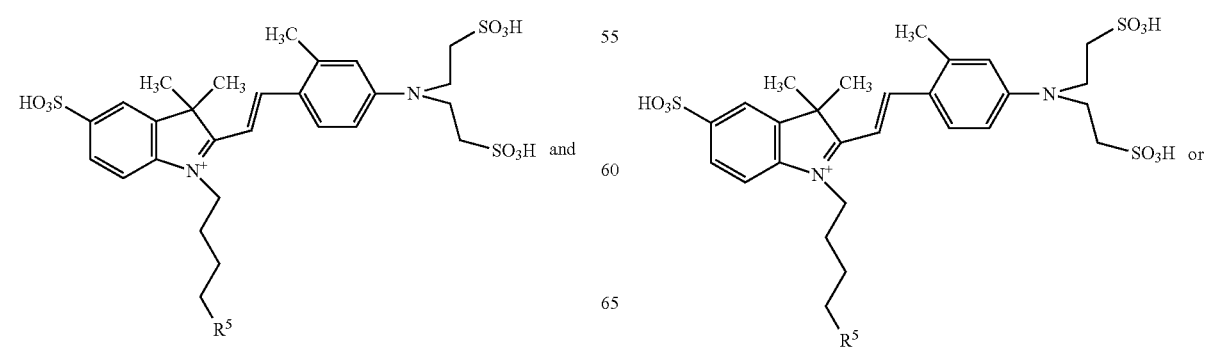

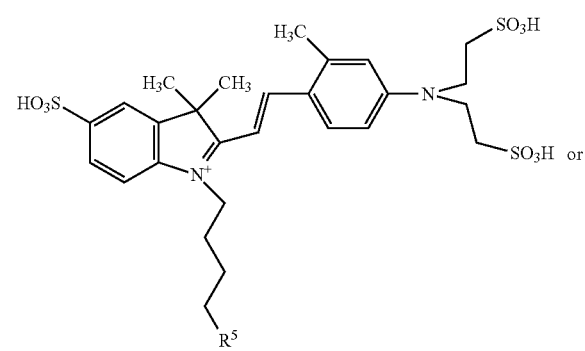

-continued
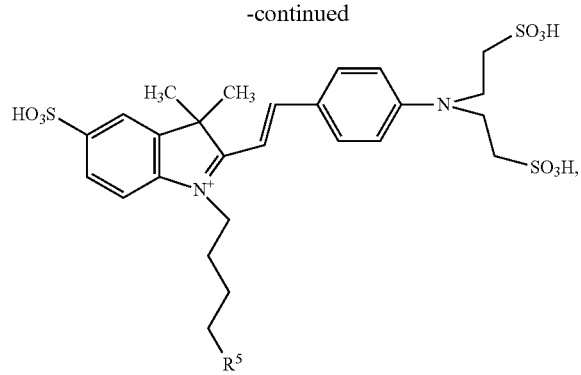
wherein R⁵ is a member selected from the group consisting of:
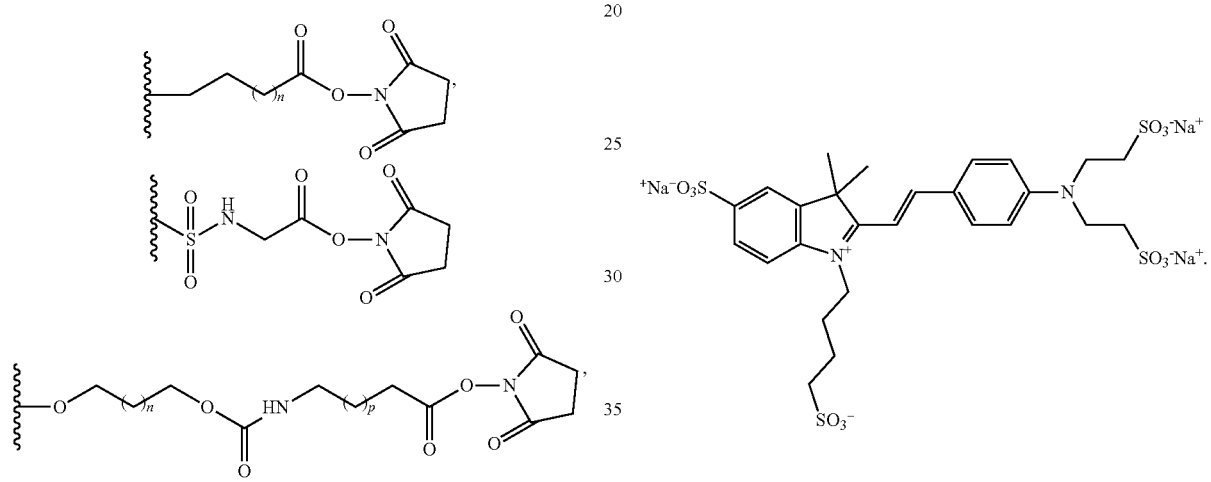
-continued
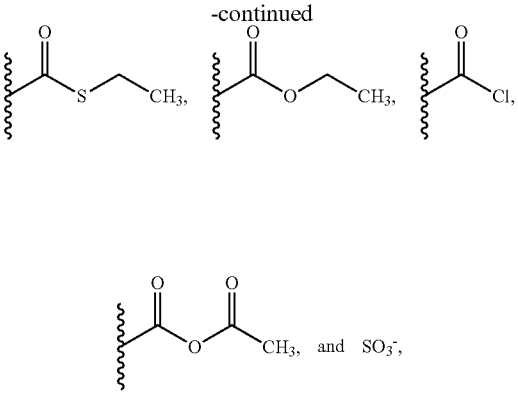
wherein n and p are each independently 0, 1, 2 or 3.
19. A compound having the formula:
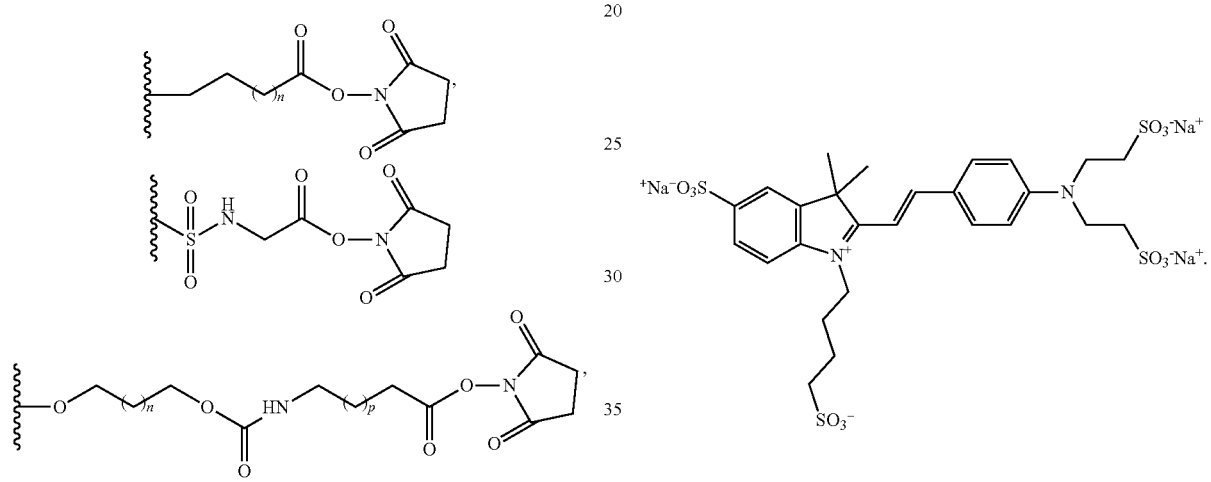
* * * * *